(12) United States Patent
Rheinheimer et al.

(10) Patent No.: US 7,663,001 B2
(45) Date of Patent: Feb. 16, 2010

(54) PREPARATION OF ISOXAZOLIN-3-YLACYLBENZENE

(75) Inventors: Joachim Rheinheimer, Ludwigshafen (DE); Wolfgang von Deyn, Neustadt (DE); Joachim Gebhardt, Wachenheim (DE); Michael Rack, Heidelberg (DE); Rene Lochtman, Mannheim (DE); Norbert Götz, Worms (DE); Michael Keil, Freinsheim (DE); Matthias Witschel, Ludwigshafen (DE); Helmut Hagen, Frankenthal (DE); Ulf Miβlitz, Neustadt (DE); Ernst Baumann, Dudenhofen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/684,630

(22) Filed: Mar. 11, 2007

(65) Prior Publication Data

US 2007/0161800 A1    Jul. 12, 2007

Related U.S. Application Data

(62) Division of application No. 10/417,083, filed on Apr. 17, 2003, now Pat. No. 7,309,802, which is a division of application No. 10/180,608, filed on Jun. 27, 2002, now Pat. No. 6,608,209, which is a division of application No. 09/674,535, filed as application No. PCT/EP99/03006 on May 4, 1999, now Pat. No. 6,525,204.

(30) Foreign Application Priority Data

May 11, 1998 (DE) ................. 198 20 722
Nov. 12, 1998 (DE) ................. 198 52 095

(51) Int. Cl.
C07C 239/08 (2006.01)
(52) U.S. Cl. .................................... 564/300
(58) Field of Classification Search .................. 564/300
See application file for complete search history.

(56) References Cited

U.S. PATENT DOCUMENTS

| | | | |
|---|---|---|---|
| 4,104,379 A | 8/1978 | Gallagher et al. | 424/244 |
| 4,582,849 A | 4/1986 | Marzolph et al. | 514/425 |
| 4,924,002 A | 5/1990 | Kostlan | 548/206 |
| 5,527,917 A | 6/1996 | Känel et al. | 548/207 |
| 5,686,434 A | 11/1997 | Kleinman | 514/92 |
| 5,846,907 A | 12/1998 | Von Deyn et al. | 504/221 |
| 5,856,504 A | 1/1999 | Kagano et al. | 548/207 |
| 6,004,903 A | 12/1999 | Von Deyn et al. | 504/239 |
| 6,124,469 A | 9/2000 | Rheinheimer et al. | 548/240 |
| 6,165,944 A | 12/2000 | Von Deyn et al. | 504/271 |
| 6,359,143 B1 | 3/2002 | Adachi et al. | 548/247 |
| 2002/0025910 A1 | 2/2002 | Von Deyn et al. | 504/263 |

FOREIGN PATENT DOCUMENTS

| | | |
|---|---|---|
| DE | 107 095 | 9/1898 |
| DE | 94177 | 12/1972 |
| DE | 094177 | * 12/1972 |
| DE | 32 22 152 | 12/1982 |
| EP | 0 609 032 | 8/1994 |
| GB | 777546 | 6/1957 |
| WO | WO 96/17834 | 6/1996 |
| WO | WO 98/31681 | 7/1998 |
| WO | WO 98/31682 | 7/1998 |
| WO | WO 99/64404 | 12/1999 |

OTHER PUBLICATIONS

Bodor et al. {CA 65:37903, 1966}.*

(Continued)

*Primary Examiner*—Laura L. Stockton
(74) *Attorney, Agent, or Firm*—Novak Druce + Quigg LLP

(57) ABSTRACT

A process is described for preparing isoxazoles of the formula I

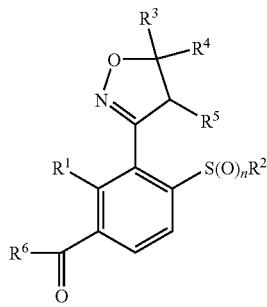

I where the substituents are as defined below:
$R^1$ is hydrogen, $C_1$-$C_6$-alkyl,
$R^2$ is $C_1$-$C_6$-alkyl,
$R^3$, $R^4$, $R^5$ are hydrogen, $C_1$-$C_6$-alkyl, or $R^4$ and $R^5$ together form a bond,
$R^6$ is a heterocyclic ring,
n is 0, 1 or 2;
which comprises preparing an intermediate of the formula VI

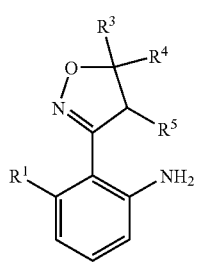

VI where R1, R3, R4 and R5 are as defined above, followed by halogenation, thiomethylation, oxidation and acylation to give compounds of the formula I.

Also novel intermediates for preparing the compounds of the formula I and novel processes for preparing the intermediates are described.

3 Claims, No Drawings

OTHER PUBLICATIONS

Bodor et al., Revue Roumaine de Chimie (1966), 11(3), pp. 393-404.*

An English translation of DD 094,177, Dec. 1972.*

Rottig, J. Prakt. Chemie 142, pp. 35-36 (1935) "Über eine einfache Synthese des antiken Purpurs".

Giam et al., J. Chem. Soc. Chem. Comm. pp. 756-757 (1980) "A simple preparation of aromatic and heteroaromatic sulphides".

Shigeru et al., Bull. Chem. Soc. JP 53(7), pp. 2023-2026 (1980) "Direct conversion of arylamides to the corresponding halides, biphenyls, and sulfides with t-butyl thionate".

Paradkar et al., J. Heterocyclic Chem. 30, pp. 1497-1500 (1993) "Reaction of b-keto ethyleneacetals with hydroxylamine: a correction".

CA Registry No. 7022-49-3, 1984.

Mamaeva et al., CA 112:157810, 1990.

Euerby et al., CA 98:52872, 1983.

Nagata, CA 71:49461, 1969.

Kaenel et al., CA 123:83358, 1995 [abstract of docment D].

Rahman et al., CA 101:6966, 1984.

Von Deyn et al., CA 129:136166, 1989 [abstract of documents J, L, and AC].

Von Deyn et al., CA 129:136165, 1998 [abstract of documents L, and AB].

Rheinheimer et al., CA 129:122657, 1998 [abstract of documents I and L].

Gallagher et al., CA 89:163433,1978 [abstract of document A].

Martani et al., CA 67:43616, 1967.

Koevendi et al., Chem. Ber., 97 (1964), pp. 1902-1909.

Lapworth, The Form of Change in organic Compounds, J. Chem. Soc. 79 (1901), pp. 1265-1284.

Das et al., Journal of Medical Chemistry, vol. 13 (1970), pp. 979-981.

* cited by examiner

PREPARATION OF ISOXAZOLIN-3-YLACYLBENZENE

This is a Divisional application of application Ser. No. 10/417,083 filed Apr. 17, 2003, now U.S. Pat. No. 7,309,802, which is a divisional application of application Ser. No. 10/180,608, filed Jun. 27, 2002 (now U.S. Pat. No. 6,608,209 B1), which is a divisional application of application Ser. No. 09/674,535 filed Nov. 2, 2000 (now U.S. Pat. No. 6,525,204 B1) which is a national stage application under 35 U.S.C. §371 of PCT/EP 99/03006 filed on May 4, 1999 (abandoned).

The present invention provides a process for preparing isoxazolin-3-ylacylbenzenes, novel intermediates and novel processes for preparing these intermediates.

Isoxazolin-3-ylacylbenzenes are useful compounds which can be used in the field of crop protection. WO 98/31681, for example, describes 2-alkyl-3-(4,5-dihydroisoxazol-3-yl) acylbenzenes as herbicidally active compounds.

It is an object of the present invention to provide an alternative process for preparing 3-heterocyclyl-substituted benzoyl derivatives. The preparation process described in WO 98/31681 for 2-alkyl-3-(4,5-dihydroisoxazol-3-yl)acylbenzenes or precursors thereof (2-alkyl-3-(4,5-dihydroisoxazol-3-yl)bromobenzene derivatives) is not particularly suitable for the industrial preparation of these compounds, since the synthesis involves a plurality of steps and the yield of the end product in question, based on the starting materials employed in the first step of the synthesis, is relatively low.

The preparation of compounds or intermediates with a structure similar to that of the compounds of the formula I is known from the literature:

WO 96/26206 discloses a process for preparing 4-[3-(4,5-dihydroisoxazol-3-yl)benzoyl]-5-hydroxypyrazoles where, in the last step, a 5-hydroxypyrazole is reacted with a 3-(4,5-dihydroisoxazol-3-yl)benzoic acid derivative. The 3-(4,5-dihydroisoxazol-3-yl)benzoic acid derivative required for this process can only be obtained with difficulty, via a large number of steps. Accordingly, the process is relatively expensive and not optimal economically.

DE 197 09 118 describes a process for preparing 3-(4,5-dihydroisoxazol-3-yl)benzoic acids starting from 3-bromo-(4,5-dihydroisoxazol-3-yl)benzene, Grignard reagents and carbon dioxide.

Surprisingly, we have found that the number of process steps in the preparation of the 3-heterocyclyl-substituted benzoyl derivatives can be reduced compared to the process described in WO 98/31681 if the synthesis is carried out via selected intermediates. Moreover, the process according to the invention has the advantage that the overall yield of the end products of the formula I and also that of the intermediates X, based on the starting materials employed, is higher than the yield of the processes described in WO 98/31681. Furthermore, the respective intermediates of the individual process steps can be obtained in good yield. Moreover, some of the individual process steps are advantageous for the industrial preparation of the intermediates, since they allow a cost-effective and economic preparation of the latter. Furthermore, it is advantageous that the starting materials used are basic chemicals which are easy to prepare and which can be obtained from several independent suppliers of raw materials, even in relatively large amounts. Overall, the process according to the invention provides a more cost-effective, economical and safe industrial process for preparing herbicidally active compounds of the formula I.

We have found that the object of the invention is achieved by a process for preparing compounds of the formula I where the substituents are as defined below:
$R^1$ is hydrogen, $C_1$-$C_6$-alkyl,
$R^2$ is $C_1$-$C_6$-alkyl,
$R^3$, $R^4$, $R^5$ are hydrogen, $C_1$-$C_6$-alkyl, or $R^4$ and $R^5$ together form a bond,
$R^6$ is a heterocyclic ring,
n is 0, 1 or 2;
which comprises preparing an intermediate of the formula VI in which $R^1$ and $R^3$-$R^5$ are as defined above.

In subsequent reaction steps, compounds of the formula VI are converted into the corresponding 3-bromo-substituted compounds (bromobenzene derivatives), and the amino group on the phenyl ring is transformed into a sulfonyl group, giving compounds of the formula X:

The compounds of the formula X (3-(4,5-dihydroisoxazol-3-yl)bromobenzenes) are useful intermediates for preparing active compounds of the formula I. In particular, the process according to the invention affords the compounds I in the last reaction step in good yield. The compounds I are suitable, for example, for use as crop protection agents, in particular as herbicides, as described in WO 96/26206 and WO 97/35850.

According to the invention, the compounds of the formula I and the required intermediates, in particular compounds of the formula VI or X, can be prepared advantageously by combining one or more of the following process steps a)-g):

a) reaction of a nitro-o-methylphenyl compound of the formula II

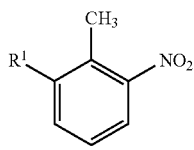

II in which the radical $R^1$ is as defined above with an organic nitrite R—ONO in the presence of a base to give an oxime of the formula III

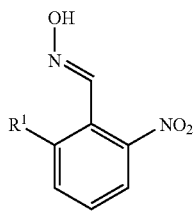

III in which the radical $R^1$ is as defined above;

b) cyclization of the oxime of the formula III with an alkene of the formula IV

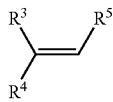

IV in which $R^3$ to $R^5$ are as defined in claim 1 in the presence of a base to give the isoxazole of the formula V

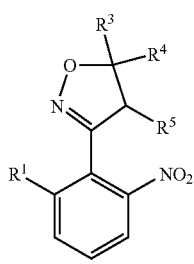

V in which $R^1$ and $R^3$ to $R^5$ are as defined in claim 1;

c) reduction of the nitro group in the presence of a catalyst to give the aniline of the formula VI

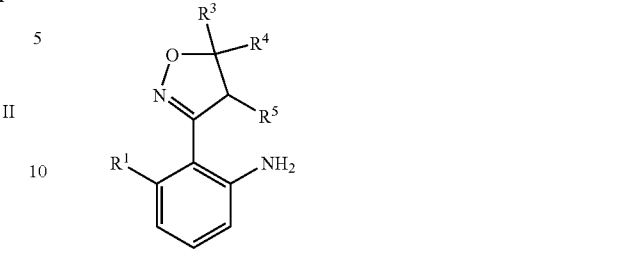

VI in which $R^1$ and $R^3$ to $R^5$ are as defined in claim 1;

d) reaction of the aniline of the formula VI with a dialkyl disulfide of the formula VII $$R^2\text{—S—S—}R^2 \qquad \text{VII}$$

in the presence of an organic nitrite R—ONO and, if appropriate, a catalyst to give the thioether of the formula VIII

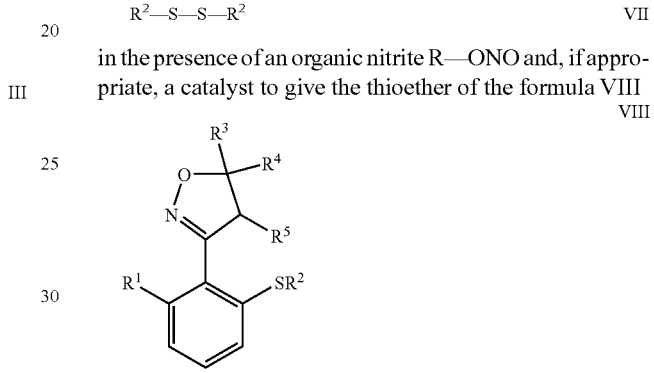

VIII in which $R^1$ to $R^5$ are as defined in claim 1;

e) bromination of the thioether of the formula VIII with a brominating agent to give the bromothioether of the formula IX

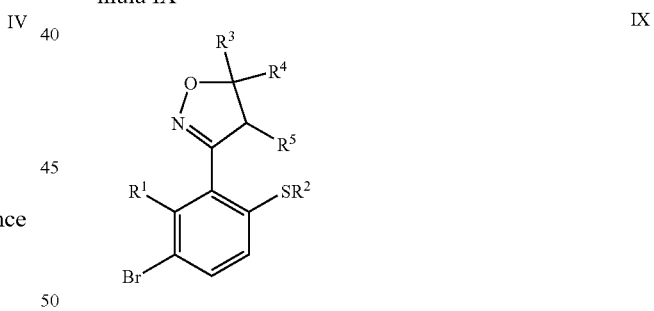

IX in which $R^1$ to $R^5$ are as defined in claim 1;

f) oxidation of the bromothioether of the formula IX with an oxidizing agent to give the isoxazoles of the formula X

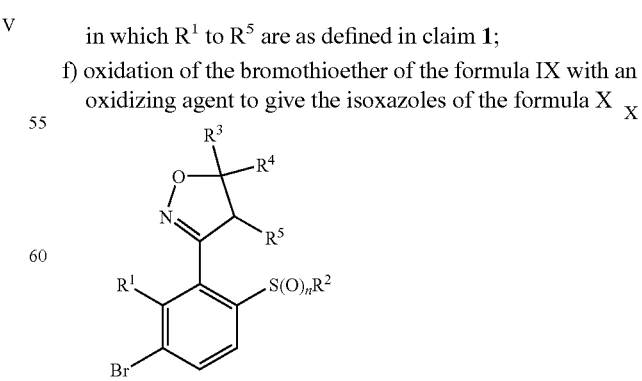

X where n is the numbers 1 or 2, g) if appropriate reacting the isoxazoline of the formula X with a compound of the formula $R^6$—OH (XI) in the presence of carbon monoxide, a catalyst and a base, to give the compounds of the formula I.

Essentially, the process according to the invention for preparing compounds X comprises one or more of the process steps a)-f) or, in the case of the compounds I, one or more of the process steps a)-g). Preference is given to those reaction sequences which comprise either one of the process steps a) or d) or else both steps a) and d).

$C_1$-$C_6$-Alkyl and $C_1$-$C_4$-alkyl are straight-chain or branched alkyl groups having 1-6 and 1-4 carbon atoms, respectively, such as, for example, methyl, ethyl, n-propyl, isopropyl, n-butyl, isobutyl, n-pentyl or n-hexyl in all cases. This applies analogously to the $C_1$-$C_6$-alkoxy group.

$R^1$ is preferably an alkyl group, in particular methyl, ethyl, isopropyl, n-propyl or n-butyl group [sic].

$R^3$, $R^4$ and $R^5$ are preferably hydrogen. $R^4$ and $R^5$ together may also denote a bond, giving rise to the corresponding isoxazole derivatives. In this case, $R^3$ is prefeerably hydrogen.

In the definition of $R^6$, "heterocyclic ring" means a saturated, unsaturated or partially unsaturated heterocycle having one, two or three oxygen, sulfur or nitrogen atoms. Preference is given to heterocycles having two nitrogen atoms. In particular, $R^6$ is a pyrazole radical, as described in more detail in WO 98/31681. It is preferably a pyrazole which is attached in the 4-position and which may be unsubstituted or substituted by further radicals which are chemically inert under the chosen reaction conditions. Suitable pyrazole substituents of this type are, for example, the following groups: hydroxyl, oxo, sulfonyloxy, $C_1$-$C_6$-alkyl or $C_1$-$C_6$-alkoxy, in particular $C_1$-$C_4$-alkyl in the 1-position. Particularly preferably, $R^6$ is the group 1-alkyl-5-hydroxypyrazol-4-yl, in particular 1-methyl-5-hydroxypyrazol-4-yl; 1-ethyl-5-hydroxypyrazol-4-yl.

The process according to the invention is particularly suitable for preparing the following compounds of the formula I:
1-methyl-4-(3-(4,5-dihydroisoxazol-3-yl)-2-methyl-4-methylsulfonylbenzoyl)-5-hydroxypyrazole,
1-ethyl-4-(3-(4,5-dihydroisoxazol-3-yl)-2-methyl-4-methylsulfonylbenzoyl)-5-hydroxypyrazole,
1-methyl-4-(3-(4,5-dihydroisoxazol-3-yl)-2-ethyl-4-methylsulfonylbenzoyl)-5-hydroxypyrazole,
1-methyl-4-(3-(4,5-dihydroisoxazol-3-yl)-2-propyl-4-methylsulfonylbenzoyl)-5-hydroxypyrazole,
1-methyl-4-(3-(4,5-dihydroisoxazol-3-yl)-2-butyl-4-methylsulfonylbenzoyl)-5-hydroxypyrazole.

Preferred intermediates of the formula VI are the following compounds:
2-(4,5-dihydroisoxazol-3-yl)aniline,
2-(4,5-dihydroisoxazol-3-yl)-3-methylaniline,
2-(4,5-dihydroisoxazol-3-yl)-3-ethylaniline,
2-(isoxazol-3-yl)-aniline,
2-(isoxazol-3-yl)-3-methylaniline,
2-(isoxazol-3-yl)-3-ethylaniline.

Preferred intermediates of the formula X are the following compounds:
3-(3-bromo-2-methyl-6-methylsulfonylphenyl)-4,5-dihydroisoxazole,
3-(3-chloro-2-methyl-6-methylsulfonylphenyl)-4,5-dihydroisoxazole,
3-(3-bromo-6-methylsulfonylphenyl)-4,5-dihydroisoxazole,
3-(3-bromo-2-ethyl-6-methylsulfonylphenyl)-4,5-dihydroisoxazole,
3-(3-bromo-2-isopropyl-6-methylsulfonylphenyl)-4,5-dihydroisoxazole,
3-(3-bromo-2-methyl-6-ethylsulfonylphenyl)-4,5-dihydroisoxazole,
3-(3-bromo-2-methyl-6-propylsulfonylphenyl)-4,5-dihydroisoxazole,
3-(3-bromo-2-methyl-6-butylsulfonylphenyl)-4,5-dihydroisoxazole,
3-(3-bromo-2-methyl-6-pentylsulfonylphenyl)-4,5-dihydroisoxazole,
3-(3-bromo-2-methyl-6-hexylsulfonylphenyl)-4,5-dihydroisoxazole.

A possible reaction sequence up to the preparation of the compounds X is summarized in the diagram below:

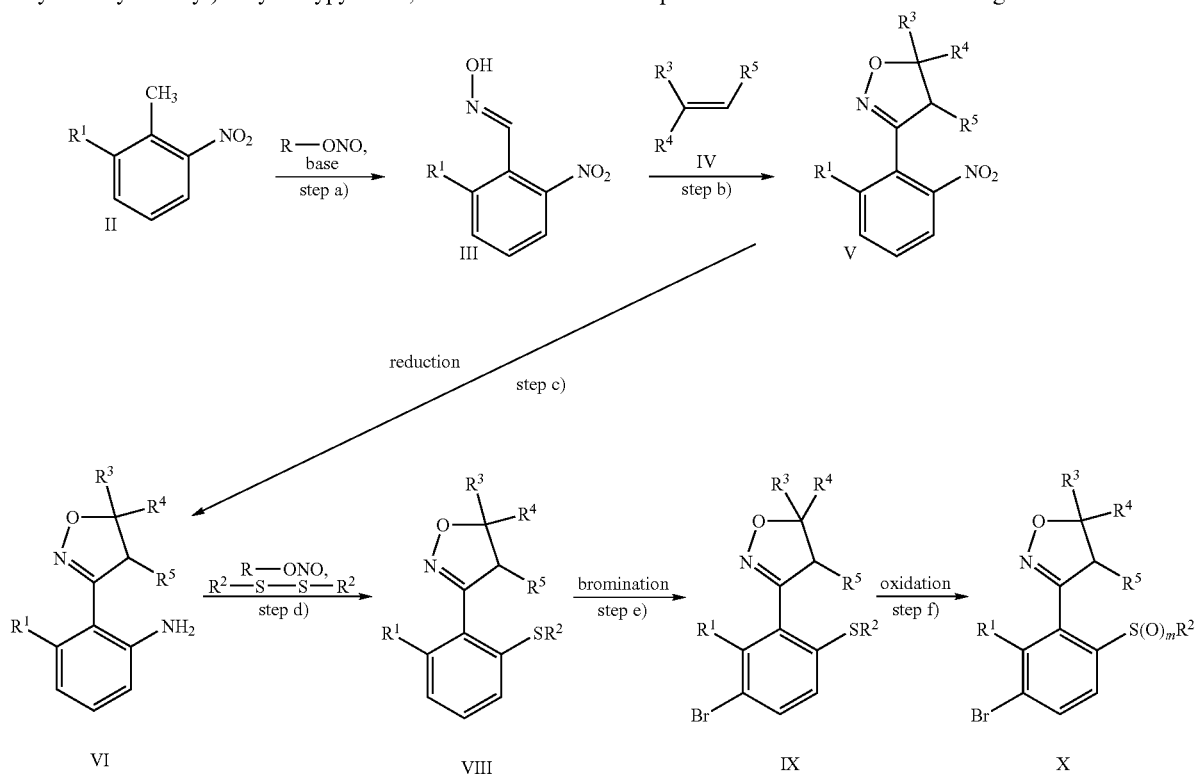

The individual reaction steps are illustrated in more detail below.

1. Step a)

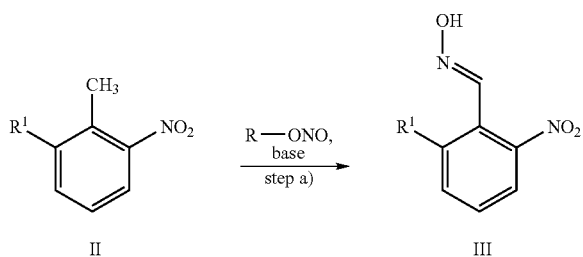

The reaction is carried out, for example under the following conditions: the solvents used are dipolar aprotic solvents, for example N,N-dialkylformamide, N,N-dialkylacetamide, N-methylpyrrolidone (NMP), preferably: dimethylformamide (DMF) or NMP. The temperature is from −60° C. to room temperature; preferably from −50 to −20° C. To achieve a sufficiently low melting point of the solvent system, it is also possible to use solvent mixtures, for example with THF. The organic nitrites R—ONO used are alkyl nitrites (R=alkyl), preferably n-butyl nitrite or (iso)amyl nitrite. Suitable bases are: MOalkyl, MOH, RMgX (M=alkali metal); preferably potassium methoxide (KOMe), sodium methoxide (NaOMe), or potassium tert-butoxide (KOtbutylate). When using sodium bases, it is possible to add 1-10 mol % of amyl alcohol. The stoichiometric ratios are, for example, as follows: 1-4 equivalents of base, 1-2 equivalents of R—ONO; preferably: 1.5-2.5 equivalents of base and 1-1.3 equivalents of R—ONO.

Addition is, for example, carried out in the following order: a) nitro-o-xylene and nitrite are initially charged and base is metered in. b) To avoid the addition of a solid base, the base can be initially charged in DMF, and nitro-o-xylene/butyl nitrite can be added simultaneously. The rate at which the base is metered in is relatively slow, so that the required cooling is reduced to a minimum. Work-up is carried out by one of the following methods: a) precipitation of the product by stirring into water. b) Precipitation of the product by adding a sufficient amount of water to the reaction mixture. Purification of the product is carried out by trituration with toluene at 0-110° C., preferably at room temperature.

2. Step b)

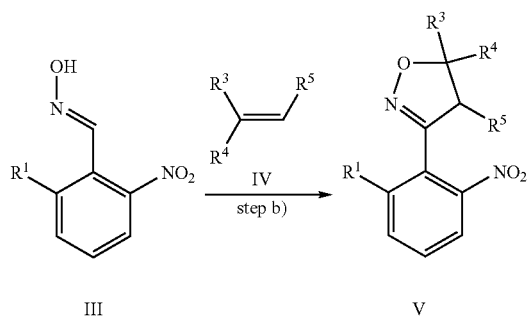

The reaction is carried out, for example, via the following mechanistic intermediates: conversion of the oxime III into an activated hydroxamic acid derivative, for example hydroxamic acid chloride, by chlorination with a chlorinating agent, conversion of the activated hydroxamic acid derivative into the nitrile oxide, for example conversion of the hydroxamic acid chloride in the presence of a base into the nitrile oxide, and subsequent cycloaddition of the alkene IV to the nitrile oxide.

This reaction is a novel process for preparing isoxazole derivatives of the formula V. Surprisingly, this process affords the isoxazolines in very good yields. Furthermore, only few byproducts are formed, and these can furthermore be removed relatively easily. Accordingly, on an industrial scale, it is easy to isolate and purify the end products, so that the isoxazolines can be prepared with high purity and at low cost. The use of known processes for preparing isoxazolines has hitherto been disadvantageous, since the isoxazolines could only be obtained in unsatisfactory yields starting from the reaction of the benzaldoximes. Furthermore, the processes known from the prior art frequently use alkali metal hypohalide-containing solutions which lead to the formation of poorly soluble and environmentally unfriendly byproducts. The process according to the invention is characterized in that the use of alkali metal hypohalide-containing solutions can be dispensed with, the process thus being essentially alkali metal hypohalide-free.

The isoxazolines are prepared, for example, by the following method: initially, hydroxamic acid chloride is formed which, in a second step, is cyclized with an alkene with metered addition of base and, if appropriate, under superatmospheric pressure. Advantageously, these individual steps can also be combined in a "one-pot" reaction. To this end, the reaction is carried out in a solvent suitable for both partial steps, for example a carboxylic ester, such as ethyl acetate, chlorobenzene or acetonitrile.

The preparation of hydroxamic acid chlorides with N-chlorosuccinimide in DMF is known from the literature (Liu et al., J. Org. Chem. 1980; 45: 3916-3918). However, it is also mentioned that the conversion of o-nitrobenzaldoximes into the hydroxamic acid chlorides by chlorination is possible only with poor yields (Chiang, J. Org. Chem. 1971, 36: 2146-2155). An expected side-reaction is the formation of benzal chloride. Surprisingly, in the process described above, conditions were found which permit the preparation of the desired hydroxamic acid chlorides in excellent yields. It is particularly advantageous that cheap chlorine is used.

The reaction is carried out, for example, under the following conditions: solvent: haloalkanes, such as 1,2-dichloroethane or methylene chloride; aromatic compounds, such as benzene, toluene, chlorobenzene, nitrobenzene or xylene; polar aprotic solvents, for example N,N-dialkylformamides, -acetamides, N-methylpyrrolidone, dimethylpropyleneurea; tetramethylurea, acetonitrile, propionitrile; alcohols, such as methanol, ethanol, n-propanol or isopropanol; carboxylic acids, such as acetic acid or propionic acid; carboxylic esters, such as ethyl acetate. Preference is given to using the following solvents: acetic acid, methanol, ethanol, 1,2-dichloroethane, methylene chloride, chlorobenzene or ethyl acetate. The reaction is carried out at from −40° C. to 100° C., preferably from −10 to 40° C. or from 0 to 30° C. Suitable for use as halogenating agents are: N-chlorosuccinimide, elemental chlorine, preferably chlorine. The stoichiometric ratios are, for example, 1-3 equivalents of halogenating agent, preferably 1-1.5 equivalents. In the case of chlorine, the metered addition is carried out by introducing chlorine gas, and N-chlorosuccinimide (NCS) is metered in as a solid or, if appropriate, in a suitable solvent.

Work-up is carried out, for example, according to the following scheme: a) no purification. The solution is directly employed further; b) solvent exchange by distillative removal of the solvent; c) addition of water and extraction of the hydroxamic acid chloride with a suitable solvent.

By adding bases, the hydroxamic acid chlorides are converted into the nitrile oxides. Since the latter compounds are unstable, the problem which had to be solved was to find conditions under which the nitrile oxides were stabilized and converted into the desired products. Surprisingly, this problem was solved by selecting the following reaction conditions: the solvents used are: halogenated alkanes, such as 1,2-dichloroethane or methylene chloride; aromatic compounds, such as benzene, toluene, chlorobenzene, nitrobenzene or xylene; polar aprotic solvents, for example N,N-dialkylformamides, -acetamides, N-methylpyrrolidone, dimethylpropyleneurea; tetramethylurea, acetonitrile, propionitrile, carboxylic esters, such as ethyl acetate. Preference is given to using: 1,2-dichloroethane, methylene chloride, toluene, xylene, ethyl acetate or chlorobenzene.

The temperatures for the reaction are from 0° C. to 100° C., preferably 0-50° C. or 0-30° C.

The bases used are: tertiary amines, for example triethylamine, cyclic amines, such as N-methylpiperidine or N,N'-dimethylpiperazine, pyridine, alkali metal carbonates, for example sodium carbonate or potassium carbonate, alkali metal bicarbonates, for example sodium bicarbonate or potassium bicarbonate, alkaline earth metal carbonates, for example calcium carbonate, alkali metal hydroxides, for example sodium hydroxide or potassium hydroxide. Preference is given to using: triethylamine, sodium carbonate, sodium bicarbonate or sodium hydroxide.

The stoichiometric ratios are, for example, 1-3 equivalents of base, preferably 1-1.5 equivalents; 1-5 equivalents of alkene, preferably 1-2 equivalents. Metered addition is preferably carried out under a superatmospheric alkene pressure, by slowly adding the base. The reaction is carried out at from atmospheric pressure to 10 atm, preferably at a pressure of 1-6 atm atmospheric pressure.

3. Step c)

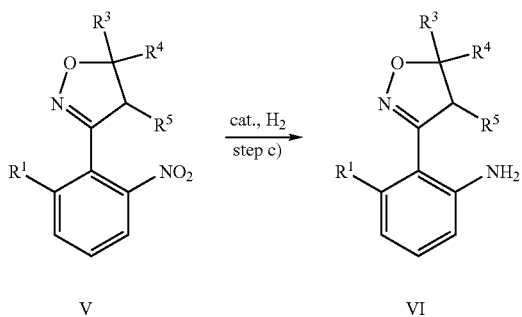

This reaction is a novel, hitherto unknown chemoselective hydrogenation of a nitro group in the presence of an isoxazoline. Surprisingly, it has been found that, under the chosen reaction conditions, the N—O bond of the isoxazoline ring is not cleaved. Catalytic hydrogenation of aromatic nitro compounds to give the anilines has been known for a long time (see Houben-Weyl, Vol. IV/1c, p. 506 ff). On the other hand, it is also known that the N—O bond of isoxazoline can be cleaved by catalytic hydrogenation, for example using Raney nickel (Curran et al., Synthesis 1986, 312-315) or palladium (Auricchio et al., Tetrahedron, 43, 3983-3986, 1987) as catalyst.

The reaction is carried out, for example, under the following conditions: suitable solvents are aromatic compounds, such as benzene, toluene, xylene; polar aprotic solvents, for example N,N-dialkylformamides, -acetamides, N-methylpyrrolidone, dimethylpropyleneurea; tetramethylurea, carboxylic esters, such as ethyl acetate, ethers, such as diethyl ether or methyl tert-butyl ether, cyclic ethers, such as tetrahydrofuran or dioxane; alcohols, such as methanol, ethanol, n-propanol or isopropanol, carboxylic acids, such as acetic acid or propionic acid. Preference is given to using the following solvents: ethyl acetate, toluene, xylene, methanol. The reaction is carried out at temperatures of from −20° C. to 100° C.; preferably of from 0 to 50° C., particularly preferably of from 0 to 30° C. The catalyst used is a platinum or palladium catalyst supported on activated carbon, with a content of from 0.1 to 15% by weight, based on the support of activated carbon. If a palladium catalyst is used, it can be doped with sulfur or selenium to achieve better selectivity. Preference is given to using platinum/activated carbon or palladium/activated carbon having a Pt— or Pd— content of 0.5-10% by weight.

The stoichiometric ratios for the reaction are, for example, as follows: from 0.001 to 1% by weight of platinum or palladium, based on the nitro compounds: preferably from 0.01 to 1% by weight of platinum. Hydrogen is metered in continuously or batchwise, preferably batchwise, at a pressure of from atmospheric pressure to 50 atm, preferably from atmospheric pressure to 10 atm.

The reaction mixture is worked up by removing the catalyst by filtration. If appropriate, the catalyst can also be re-used. The solvent is distilled off. For the subsequent reaction in the next process step, the product can be employed directly without further purification. If required, the product can also be purified further. The product is purified, for example, according to the following scheme: if required, the aniline can be purified by taking it up in dilute mineral acid, for example aqueous hydrochloric acid or dilute sulfuric acid, and extraction with a suitable organic extractant, for example halogenated alkanes, such as 1,2-dichloroethane or methylene chloride, aromatic compounds, such as benzene, toluene, chlorobenzene or xylene, ethers, such as diethyl ether or methyl tert-butyl ether, or carboxylic esters, such as ethyl acetate, and be liberated again using a base.

4. Step d)

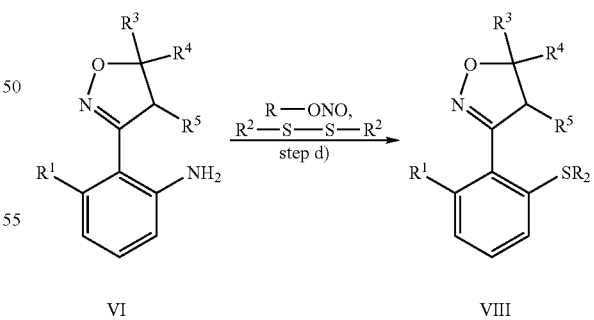

The reaction is carried out under the following conditions: the solvents used are, for example: halogenated alkanes, such as 1,2-dichloroethane or methylene chloride, aromatic compounds, such as benzene, toluene, chlorobenzene, nitrobenzene, or an excess of the dialkyl disulfide as solvent. Preference is given to using excess dialkyl disulfide as solvent. The temperature for the reaction is from 40° C. to 150° C., preferably from 50 to 100° C., particularly preferably from 60 to 90° C. The reagents used are organic nitrites (R—ONO), such as, for example, alkyl nitrites, preferably n-butyl nitrite, (iso) amyl nitrite or tert-butyl nitrite. Here, R is any organic, chemically inert radical which does not have any effect on the actual reaction. R is, for example, a $C_1$-$C_6$-alkyl or $C_2$-$C_6$-alkenyl group.

In the reaction of the compounds, the stoichiometric ratios are, for example, as follows: 1-3 equivalents of alkyl nitrite, preferably 1-1.5 equivalents of alkyl nitrite. The following catalysts may be used: copper powder, elemental copper in a different form, such as, for example, turnings, wire, granules, pellets, rods; copper(I) salts, for example copper(I) chloride, copper(I) bromide or copper(I) iodide, copper(II) salts, or elemental iodine, particularly preferably copper powder. When carrying out the reaction in the solvent, 1-3 equivalents of dialkyl disulfide, preferably 1-2 equivalents, are employed. In a preferred embodiment, an excess of dialkyl disulfide is employed as solvent and then recovered by distillation. For further reactions, the product can be used without further purification. If appropriate, it is also possible to purify the product beforehand by distillation or crystallization using suitable solvents, for example from diisopropyl ether.

5. Step e)

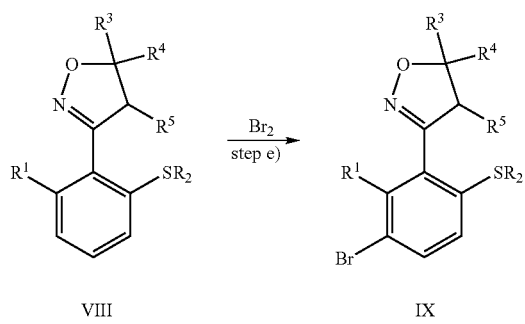

VIII                 IX

The bromination is carried out similarly to the method described in WO 98/31676. Acetic acid is an advantageous solvent.

6. Step f)

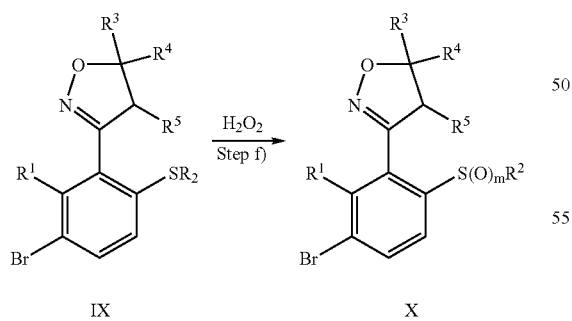

IX                 X

The oxidation is carried out similarly to the method described in WO 98/31676 (cf. p. 8, line 32 to p. 11, line 25).

7. Step g)

The optional subsequent conversion of the compound of the formula X into compounds of the formula I is carried out by adding $R^6$—OH (XI) in the presence of carbon monoxide and a suitable catalyst and a base. If $R^6$ is an unsubstituted or substituted pyrazole or pyrazolone ring, the reaction is preferably carried out using palladium-containing catalysts, such as, for example, Pd(0) catalyst or bis(triphenylphosphine) palladium(II) chloride.

The process mentioned in step g) is a novel and advantageous process for preparing compounds of the formula I which are obtained starting from halophenyl derivatives X by acylation or carboxylation with hydroxy-substituted heterocycles of the formula $R^6$—OH (XI).

EP-A 344 775 discloses a process for preparing 4-benzoyl-5-hydroxypyrazoles in one step where the synthesis is carried out starting from bromobenzenes and 5-hydroxypyrazoles in the presence of carbon monoxide, base and catalyst. The benzoyl radical of the target molecules may carry the following substituents in the 3-position: alkoxycarbonyl, alkoxy, alkoxymethyl. These substituents are considered to be relatively stable or inert chemically and allow the use of the drastic reaction conditions of the working examples. In contrast, the preparation of benzoyl-5-hydroxypyrazoles which carry less stable substituents in the 3-position, as is the case, for example, for the isoxazole or isoxazoline radical, are not described in EP 344 775, with respect to the drastic reaction conditions. In particular, owing to its redox properties, the isoxazole or isoxazoline radical is considered to be a highly sensitive radical. A further disadvantage of the process known from EP-A 344 775 is the fact that the 5-hydroxypyrazole is always employed in a large excess.

Below, the process is illustrated in more detail, using the example where $R^6$=pyrazole (XI.a) as heterocycle. However, in principle, it is also possible to use other heterocyclic compounds, as defined at the outset.

The process is preferably carried out by reacting a hydroxypyrazole of the formula XI.a

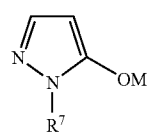

XI.a in which $R^7$ is $C_1$-$C_6$-alkyl and M is hydrogen or an alkali metal atom, preferably sodium or potassium, and a bromobenzene of the formula X

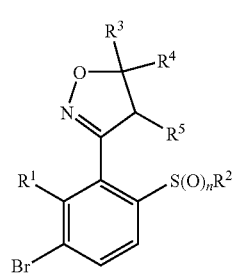

X in which $R^1$ to $R^5$ are as defined above, in the presence of carbon monoxide, a palladium catalyst, if appropriate at least one molar equivalent of a potassium salt and if appropriate at least one molar equivalent of a tertiary amine of the formula XIII $N(R_a)_3$               XIII in which one of the radicals $R_a$ may represent phenyl or naphthyl and the other radicals $R_a$ are $C_1$-$C_6$-alkyl, at temperatures of from 100 to 140° C. and a pressure of from 1 to 40 kg/cm².

In a preferred embodiment of the process, the 5-hydroxypyrazole XI.a and the bromobenzene derivative X are employed in a molar ratio of from 1 to 2.

Preference is given to using, as 5-hydroxypyrazole XI.a, compounds in which $R^7$ is $C_1$-$C_6$-alkyl, in particular methyl or ethyl.

The 5-hydroxypyrazoles (or pyrazolinones) of the formula XI.a used as starting materials are known and can be prepared by processes known per se (cf. EP-A 240 001, WO 96/26206 and J. Prakt. Chem. 315 (1973), 382).

In general, the 5-hydroxypyrazole XI.a is employed in equimolar amounts or in excess, based on the bromobenzene derivative X. For reasons of economy, it makes sense to avoid a relatively large excess of 5-hydroxypyrazole. Under the reaction conditions according to the invention, the stoichiometric reaction gives the same yield as that which is obtained if an excess of 5-hydroxypyrazole is used. This was surprising, since a large excess of 5-hydroxypyrazole is used in all of the examples of the process described in EP-A 344 775. In the process according to the invention, the molar ratio of 5-hydroxypyrazole to bromobenzene is preferably adjusted to 1-2 and particularly preferably to 1.0-1.2.

Above 140° C., decomposition occurs, and below 100° C., the reaction comes to a halt. The reaction is therefore generally carried out in a temperature range of from 100 to 140° C., preferably from 110 to 130° C.

Surprisingly, it has been found that the high pressure in the range of up to 150 kg/cm² normally required for the reaction (cf. the details given in EP 344 775) can be reduced to a value of at most up to 40 kg/cm², preferably to up to 20 kg/cm² or else up to 10 kg/cm², without this having an adverse effect on the reaction conditions, such as reaction temperature or reaction time, or resulting in a loss of yield. The reaction pressure is preferably at least 3 kg/cm², in particular at least 5 kg/cm². Suitable pressure ranges are, for example: 1-40 kg/cm², 5-20 kg/cm² or 10-20 kg/cm², in particular 3-10 and particularly preferably 5-8 kg/cm².

This pressure reduction is particularly advantageous if the preparation process is to be carried out on an industrial scale, since the safety requirements which have to be met with respect to the pressure vessels used are less stringent. Thus, the costly use of high-pressure vessels can be dispensed with. Accordingly, the preparation process described in g) is safer and more economical.

Furthermore, it has surprisingly been found that the palladium compounds used as catalysts are, under the chosen reaction conditions, mainly obtained as elemental palladium and can be removed from the reaction mixture in a simple manner by filtration. Thus, concentration of the palladium-containing reaction solution for subsequent disposal, which is complicated and costly, and any incineration of the residues can substantially be dispensed with. This reduces recycling costs. The pore size of the precipitated palladium is 1-10 μm, in particular 1-4 μm. The palladium filtered off in this way can be worked up at low cost to give the corresponding palladium compounds, such as, for example, palladium chloride, since the recycling costs depend on the palladium concentration.

Suitable solvents for the reaction in process step g) are nitriles, such as benzonitrile and acetonitrile, amides, such as dimethylformamide, dimethylacetamide, tetra-$C_1$-$C_4$-alkylureas or N-methylpyrrolidone, and preferably ethers, such as tetrahydrofuran and methyl tert-butyl ether. Particularly preferred solvents are ethers such as 1,4-dioxane and dimethoxyethane.

Suitable catalysts are palladium-ligand complexes in which the palladium is present at the oxidation state 0, metallic palladium, if appropriate on a support, and preferably palladium(II) Salts. The reaction with palladium(II) salts and metallic palladium is preferably carried out in the presence of complex ligands.

A suitable palladium(0)-ligand complex is, for example, tetrakis (triphenylphosphane)palladium.

Metallic palladium is preferably absorbed on an inert carrier, such as, for example, activated carbon, silica, alumina, barium sulfate or calcium carbonate. The reaction is preferably carried out in the presence of complex ligands, such as, for example, triphenylphosphane.

Suitable palladium(II) salts are, for example, palladium acetate and palladium chloride. The reaction is preferably carried out in the presence of complex ligands, such as, for example, triphenylphosphane.

Suitable complex ligands for the palladium-ligand complexes, or those in whose presence the reaction with metallic palladium or palladium(II) salts is preferably carried out, are tertiary phosphanes whose structure is represented by the formulae below:

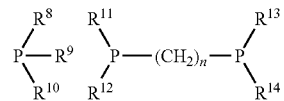

where n is a number from 1 to 4 and the radicals $R^8$ to $R^{14}$ are $C_1$-$C_6$-alkyl, aryl-$C_1$-$C_2$-alkyl or, preferably, aryl. Aryl is, for example, naphthyl and unsubstituted or substituted phenyl, such as, for example, 2-tolyl, and in particular unsubstituted phenyl.

The complex palladium salts can be prepared in a manner known per se starting from commercially available palladium salts, such as palladium chloride or palladium acetate, and the corresponding phosphanes, such as, for example, triphenylphosphane or 1,2-bis(diphenylphosphano)ethane. Many complex palladium salts are also commercially available. Preferred palladium salts are [(R)(+)2,2-bis(diphenylphosphano)-1,1'-binaphthyl]palladium(II) chloride, bis(triphenylphosphane)palladium(II) acetate and, in particular, bis(triphenylphosphane)palladium(II) chloride.

In general, the palladium catalyst is employed in a concentration of from 0.05 to 5 mol %, preferably from 1 to 3 mol %.

Amines $N(R_a)_3$ of the structure XIII which are suitable for the process are tertiary amines, such as, for example, N-methylpiperidine, ethyldiisopropylamine, 1,8-bisdimethylaminonaphthalene or, in particular, triethylamine.

Suitable potassium salts are, for example, potassium phosphate, potassium cyanide and, in particular, potassium carbonate. Advantageously, the water content of the potassium salt should be low. For this reason, the potassium carbonate was, prior to use, generally dried at least 150° C.

The amount of potassium salt used is advantageously at least 1 molar equivalent. Otherwise, the reaction rate will be reduced, or the intermediate Fries rearrangement does not proceed completely, and O-acylated pyrazole derivatives are obtained. Preferably, in each case from 2 to 4 molar equivalents and particularly preferably 2 molar equivalents of potassium salt are employed, based on the bromobenzene III.

In addition to the potassium salt, the reaction mixture is preferably also admixed with an amine $N(R_a)_3$ of the formula XIII in which one of the radicals $R_a$ may be phenyl or naphthyl and the other radicals $R_a$ are $C_1$-$C_6$-alkyl. Preferably, 1 to 4 molar equivalents, particularly preferably 2 molar equivalents, of the amine XIII are employed, based on the bromobenzene X.

For work-up, the reaction solution is usually introduced into water. If the reaction is carried out in a water-miscible solvent, such as 1,4-dioxane, it may be advantageous to remove beforehand some or all of the solvent from the reaction mixture, if appropriate under reduced pressure. Any solid components are then removed from the aqueous alkaline reaction mixture, and a pH of from 2.5 to 4.5, preferably 3.5, is established by acidification with a mineral acid, such as, for example, hydrochloric acid, resulting in virtually complete precipitation of the product of value. The isoxazoline radical, in particular, is sensitive to hydrolysis. In processes for preparing benzoylpyrazoles which contain this radical, a pH of below 2 should preferably be avoided.

The acylation in process step g) is preferably carried out under the following process conditions: solvent: dioxane or mixtures of dioxane and acetonitrile. Temperature: 110-130° C. Pressure: 5-8, preferably about 6, $kg/cm^2$. Catalyst: palladium(II) chloride. Molar ratio of the heterocyclic hydroxy compounds (such as, for example, 5-hydroxypyrazole) to bromobenzene derivatives: from 1 to 2 and particularly preferably from 1.0 to 1.2.

Alternatively to the synthesis route shown in scheme 1, the compounds of the formula X can also be prepared according to schemes 2 and 3 below.

Scheme 2 shows a possible synthesis route to bromobenzene derivatives of the type of formula X using the synthesis of 3-[3-bromo-2-methyl-6-(methylsulfonyl)phenyl]-4,5-dihydro-isoxazole as an example. The individual process steps can be carried out following customary standard methods.

Scheme 2

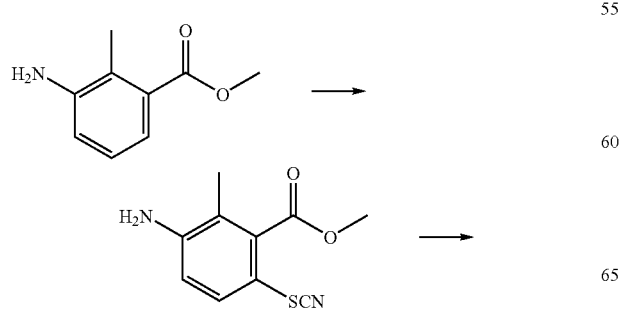

-continued

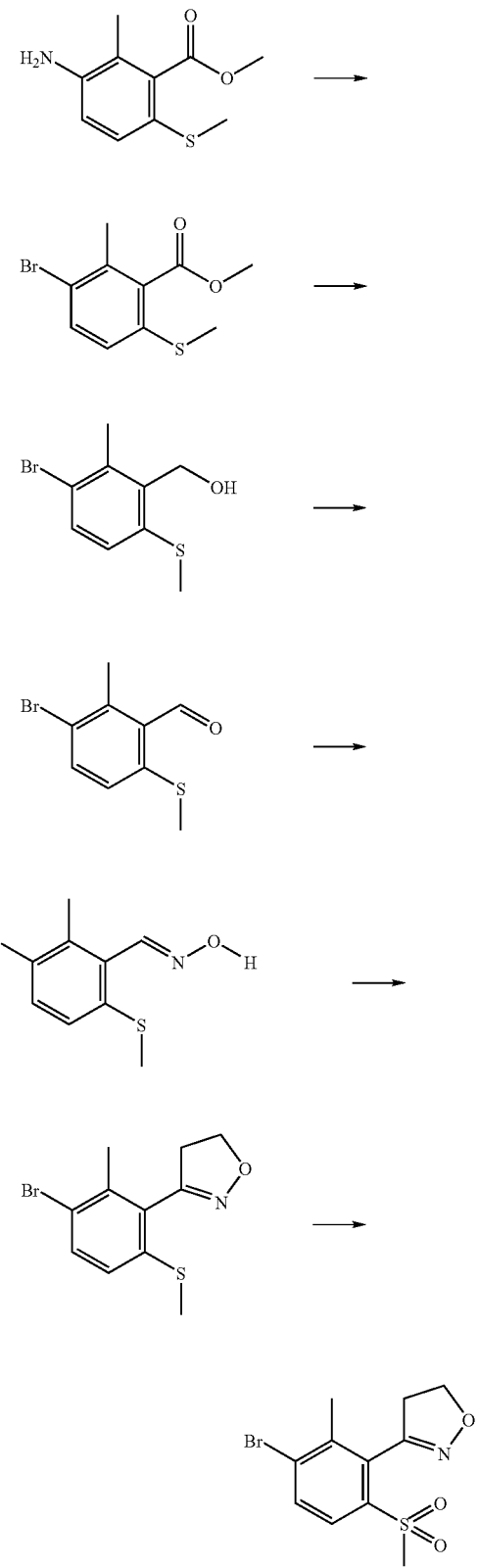

Scheme 3 shows a further possible synthesis route to bromo-benzene derivatives of the type of formula X.

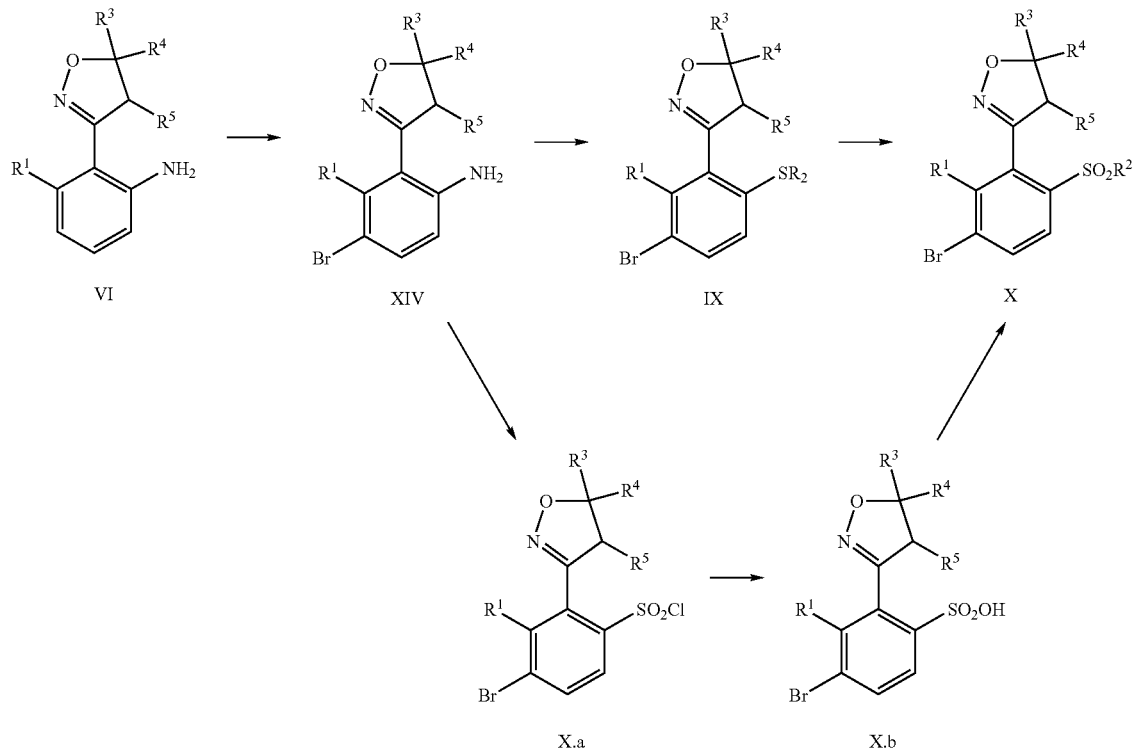

The bromination of compounds of the formula VI is carried out similarly to the direct bromination of anilines. If the reagent used is tetrabutylammonium tribromide, it is in some cases possible to achieve selective monobromination in the position para to the amine function (Berthelot et al., Synth. Commun. 1986, 16: 1641). However, a general problem in such brominations is the formation of polybrominated products (Bull. Chem. Soc. Jpn. 1988, 61: 597-599). Thus, for example, the reaction of VI with tetrabutylammonium tribromide in a methanol/water mixture with calcium carbonate as base gives a product mixture containing about 25% of dibrominated byproduct. The separation of the product mixture is critical in particular when the substituents include isoxazole or isoxazoline radicals which, with a view to their redox properties, are considered as being labile under the chosen reaction conditions.

We have now found conditions which allow the desired product XIV to be prepared in good yields, without more highly brominated byproducts being formed. According to the reaction conditions of the invention, the preferred reagent is tetrabutylammonium tribromide. The solvents used are haloalkanes, such as 1,2-dichloroethane or methylene chloride, alcohols, such as methanol, ethanol, n-propanol, isopropanol, or aliphatic nitriles, such as acetonitrile, preferably acetonitrile. The preferred base [sic] is potassium carbonate. The brominated intermediates XIV can then be converted into the isoxazol-3-ylbromobenzenes X according to the invention by various routes. The intermediates for preparing compounds IX from XIV or compounds X from IX can be prepared by the processes already mentioned above.

However, it is alternatively also possible to convert the anilines initially into the sulfonyl chlorides X.c (see Houben-Weyl, Vol. IX, pp. 575-580). The sulfonyl chlorides can be converted by reduction, for example using sodium sulfide, via the sulfinic acid stage (see Houben-Weyl, Vol. IX, pp. 306-307) and subsequent alkylation (see Houben-Weyl, Vol. IX, pp. 231-233), into the alkyl sulfones. The two steps can advantageously be combined in a "one-pot reaction". This synthesis has the advantage that favorable starting materials are used for introducing the alkylsulfonyl groups.

The oximation of substituted toluenes, used in process step a) of the process according to the invention, is a novel and advantageous method for converting toluene derivatives into benzaldoximes. In principle, this method is suitable for preparing benzaldoximes of the formula XV

XV

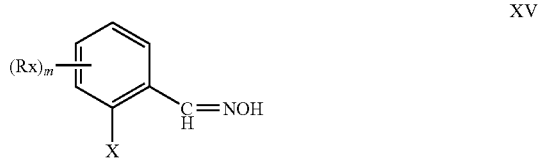

in which the radicals are as defined below:
X is $NO_2$, $S(O)_n Ry$,
Rx is any inert radical;
Ry is any inert radical;
m is 0, 1, 2, 3 or 4,
n is 0, 1 or 2.

Rx and Ry are any organic radicals which can be identical or different and are inert under the chosen reaction conditions. Rx may, for example, be: halogen, such as, for example, chlorine, bromine or iodine; carboxyl; carboxamide; N-alkylcarboxamides and N,N-dialkylcarboxamides; phenyl; $C_1$-$C_6$-alkyl, such as, for example, methyl, ethyl; $C_1$-$C_6$-alkoxy; $C_1$-$C_6$-alkylthio or other radicals. If m>1, Rx can in each case be identical or different. Rx preferably has the same meaning as $R^1$ and is located ortho to the oxime group —CH═NOH. m is, in particular, the number 2, one of the substituents Rx having the same meaning as $R^1$ and the second substituent Rx being a halogen atom which is preferably located meta to the oxime group. Ry is preferably $C_1$-$C_6$-alkyl, for example methyl, ethyl, propyl.

Preferred compounds XV are those in which X is the group $SO_2$-Ry and m is the number 2. In this case, one of the radicals Rx is preferably halogen (for example bromine or chlorine) and is located meta to the oxime group. The second radical Rx is preferably $C_1$-$C_6$-alkyl (for example methyl, ethyl) and is located ortho to the oxime group.

According to the invention, compounds of the formula XVI (o-nitrotoluene or o-alkylsulfonyltoluene)

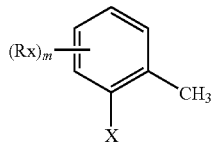

XVI in which the substituents are as defined above are reacted with an organic nitrite of the formula R—O—NO, as already defined, in the presence of a base.

The nitrosation of o-nitrotoluene has been described in the literature (Lapworth, J. Chem. Soc. 79 (1901), 1265). However, even in this early work, a dimeric byproduct is mentioned. Later works only describe the preparation of dimeric products under similar reaction conditions (Das et al., J. Med. Chem. 13 (1970), 979). Repetition of the experiment described in the literature using o-nitrotoluene shows that, indeed, the 2-nitrobenzaldoxime is formed in small amounts.

When the conditions described were applied to 3-nitro-o-xylene, only the dimer XVIII was formed.

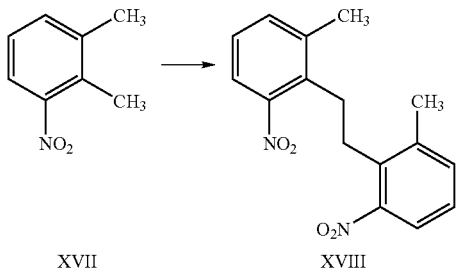

XVII        XVIII

For Michael additions, which proceed under similar conditions, the literature likewise mentions that they do not succeed with 3-nitro-o-xylene (Li, Thottathil, Murphy, Tetrahedron Lett. 36 (1994), 6591). From what has been described, it would therefore not be expected that benzaldoximes can be prepared in excellent yields from 6-substituted 2-nitrotoluene. Moreover, it has surprisingly been found that alkylsulfonates (X═$SO_2$Ry) can, under comparable conditions, likewise be oximated at the methyl group in the opposition. The compounds prepared by the process according to the invention are important intermediates in the production of active compounds for crop protection agents (WO 98/31681).

The reaction is preferably carried out under the following conditions:

The solvents used are: dipolar aprotic solvents, for example N,N-dialkylformamide, N,N-dialkylacetamide, N-methylpyrrolidone, preferably DMF, NMP. The temperature is from −60° C. to room temperature; preferably from −50 to −20° C. The preferred nitrite or alkylnitrite is n-butyl nitrite and (iso)amyl nitrite. Suitable bases are: (M═alkali metal): MOalkyl, MOH, RMgX; preferably KOMe, NaOMe, KOt-butoxide. If sodium bases are employed, preference is given to adding 1-10 mol % of amyl alcohol. The stoichiometry is as follows: 1-4 equivalents of base, 1-2 equivalents of RONO; preferably: 1.5-2.5 equivalents of base, 1-1.3 equivalents of RONO (i.e. an organic nitrite). The order of addition: a) nitro-o-xylene and nitrite are initially charged and base is metered in. b) To avoid having to meter in the base as a solid, it is possible to initially charge the base in DMF and to add nitro-o-xylene/butyl nitrite simultaneously. It is advantageous to meter in the base over a relatively long period of time, to reduce the required cooling.

Work-up is carried out, for example, as follows: a) precipitation by stirring the mixture into water/acid. b) Precipitation by adding a sufficient amount of water/acid. Suitable acids are mineral acids, such as sulfuric acid, hydrochloric acid or phosphoric acid, or else carboxylic acids, such as acetic acid. Purification of the product: by trituration with toluene at from 0 to 110° C., preferably at room temperature.

If the reaction is carried out at a relatively high temperature (from −10 to 0° C.), followed by additional stirring at room temperature, work-up affords the benzonitriles directly. Furthermore, it is possible to release the aldehyde function from the benzaldoximes of the formula XV in the presence of an acidic catalyst and an aliphatic aldehyde, for example aqueous formaldehyde solution. Suitable solvents are halogenated alkanes, such as 1,2-dichloroethane or methylene chloride, aromatic compounds, such as benzene, toluene, chlorobenzene, nitrobenzene or xylene, polar aprotic solvents, for example N,N-dialkylformamides, -acetamides, N-methylpyrrolidone, dimethylpropyleneurea; tetramethylurea, tetrahydrofuran, acetonitrile, propionitrile or acetone, if appropriate with addition of water. Particularly advantageous are aqueous acetone (1 to 20% of water), dioxane/water mixtures and tetrahydrofuran/water mixtures. The reaction is carried out at temperatures from room temperature to the reflux temperature of the solvent, preferably from 30 to 70° C. Suitable acids are mineral acids, such as aqueous hydrochloric acid, sulfuric acid or phosphoric acid, and acidic ion exchangers, such as Amberlyst 15 or Dowex 50W×8.

In the case of the compounds of the formula XV, the oxime group —CH═NOH can then be converted into the corresponding aldehydes (—CHO) or else into the corresponding nitrites (—CN). These compounds are important synthesis building blocks for preparing active compounds of the formula I (cf. WO 98/31681).

The thioalkylation step employed in process step d) of the process according to the invention is a novel and advantageous method for converting aniline derivatives into thioether derivatives (thioalkylation of aniline derivatives). In principle, the method is generally suitable for preparing thioethers of the formula XIX

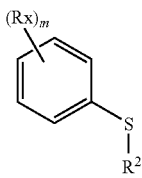

where Rx is any inert radical, m is a number from 0 to 5 and $R^2$ is a $C_1$-$C_6$-alkyl group, which comprises reacting an aniline of the formula XX

with a dialkyl disulfide of the formula VII

in the presence of a catalyst. Preferred catalysts are copper powder, in particular copper powder having a particle size of below 70 μm, or elemental copper in another form, such as, for example, turnings, wire, granules, pellets or rods.

In the compounds of the formula XIX and XX, Rx is any radical which is chemically inert under the chosen reaction conditions during the reaction with compounds of the formula VII. In this sense, suitable Rx groups are, for example: hydrogen, alkyl, haloalkyl, halogen, cyano, nitro, alkoxy, haloalkoxy, alkylthio or heterocyclic radicals as mentioned at the outset in the definition of $R^6$. A heterocyclic radical is, in particular, an unsubstituted or alkyl-substituted 5-membered heterocyclic saturated, partially saturated or aromatic ring from the group of the isoxazolines, isoxazoles, thiazolines, thiazoles, oxazoles and pyrazoles. The compounds of the formula XIX and XX may carry one or more, preferably one, two or three, substituents Rx, which may be identical or different.

Rx is preferably a $C_1$-$C_6$-alkyl group, for example methyl, ethyl or propyl. m is preferably the number 1 or 2. If m is the number 1, Rx is preferably ortho or meta to the group —S—$R^2$ (in the case of compounds XIX) or to the amino group (in the case of the compounds XX). If m is the number 2, the second radical Rx is preferably ortho and meta to the group —S—$R^2$ or to the amino group.

Thioethers of the formula XIX are useful intermediates for preparing active compounds in the chemical industry, for example for preparing crop protection agents (for example WO 96/11906; WO 98/31676) or for preparing medicaments. A process which is frequently used for introducing alkylthio functions is the exchange of a halogen (EP 0 711 754). However, the process described in this publication has the disadvantage that it is limited to aromatic compounds which are substituted by radicals which are strongly electron-withdrawing. Moreover, the preparation frequently requires high temperatures. Under these reaction conditions, other sensitive functional groups are chemically modified, resulting in complex reaction mixtures which are difficult and costly to purify, or where in certain cases removal of the impurities is not possible at all. In addition, suitable precursors are not always commercially available.

Methods for preparing arylalkyl sulfides from anilines are known, but these methods have serious disadvantages. The Sandmeyer reaction, for example, requires the use of equimolar amounts of copper alkyl thiolate (Baleja, Synth. Commun. 14 (1984), 215-218). The yields that are obtained are typically only in the range of from 20 to 60%.

A further method that has been described is the reaction of aromatic amines with alkyl nitrites in excess dialkyl sulfide (Giam et al., J. Chem. Soc., Chem. Commun 1980, 756-757). Here, it is a problem that, in some cases to a considerable extent, side-reactions occur, resulting in poor yields and a high expense in the purification of the product. Moreover, it was observed that, if the reaction is carried out in an inert diluent, a very vigorous reaction which was difficult to control set in after an induction phase, thus excluding use on an industrial scale. It is an object of the present invention to provide an alternative process for the preparation of thioethers. Using the preparation process according to the invention, it is possible to prepare aromatic alkyl thioethers advantageously from anilines. Using the process, it is possible to carry out the preparation in a simple manner, at low cost and efficiently, taking into account ecologically and economically advantageous aspects.

According to the invention, the reaction of the aniline with a dialkyl disulfide and an organic nitrite R—ONO is carried out according to the reaction scheme shown above, in the presence of a catalyst, preferably elemental copper. Comparative experiments have shown that, under the conditions according to the invention, considerably better yields are obtained and fewer byproducts are formed than when no catalyst is used. Moreover, the reaction is easy to control and suitable for use on an industrial scale.

The reaction is carried out under the reaction conditions specified in more detail below: suitable solvents are halogenated alkanes, such as 1,2-dichloroethane or methylene chloride, or aromatics, such as benzene, toluene, chlorobenzene or nitrobenzene. Alternatively, it is also possible to use an excess of dialkyl disulfide itself as solvent. This variant is particularly advantageous. The temperatures for the reaction are from 40° C. to 150° C., preferably from 60 to 100° C. and in particular from 70 to 90° C. In the reaction, it is advantageous to add a $C_1$-$C_6$-alkyl nitrite reagent. Suitable for this purpose are, for example, n-butyl nitrite, (iso)amyl nitrite and tert-butyl nitrite. In this case, the stoichiometry is, for example, 1-3 equivalents of alkyl nitrite, preferably 1-1.5 equivalents of alkyl nitrite. Suitable catalysts are copper powder or elemental copper in another form, copper(I) salts, for example copper(I) chloride, copper(I) bromide or copper(I) iodide, copper(II) salts, or elemental iodine, preferably copper powder or elemental copper in another form. The reaction is, for example, carried out under the following stoichiometric ratios: if the reaction is carried out in a solvent: 1-3 equivalents of dialkyl disulfide, preferably 1-2 equivalents. If the reaction is carried out without additional solvent, i.e. if the dialkyl disulfide is used as solvent: an excess of dialkyl disulfide or of a dialkyl disulfide mixture is used, subsequent distillative recovery being possible. The product is purified, for example, by distillation or crystallization (for example from diisopropyl ether).

The present invention furthermore provides a process for preparing compounds X using the process described above for the oximation of substituted toluenes XVI (cf. process step a)) and/or using the process described above for the thioalkylation of aniline derivatives XX (cf. process step d)). In reaction scheme 4 below, a suitable preparation process is described using the example of a compound X where $R^1=CH_3$, $R^2=CH_3$, $R^3=R^4=R^5=H$. In principle, the process is also suitable for preparing compounds X where the radicals $R^1$-$R^5$ are as defined above.

EXAMPLE 1

Preparation of 2-methyl-6-nitrobenzaldoxime (Process Step a)—Variant A)

A solution of 274 g (2.6 mol) of n-butyl nitrite (97%) and 300 g (2.0 mol) of 3-nitro-o-xylene (97%) in 750 ml of dimethylformamide is cooled to from −55 to −60° C., and a solution of 522 g (4.56 mol) of potassium tert-butoxide in 750 ml of dimethylformamide is added dropwise at this tempera-

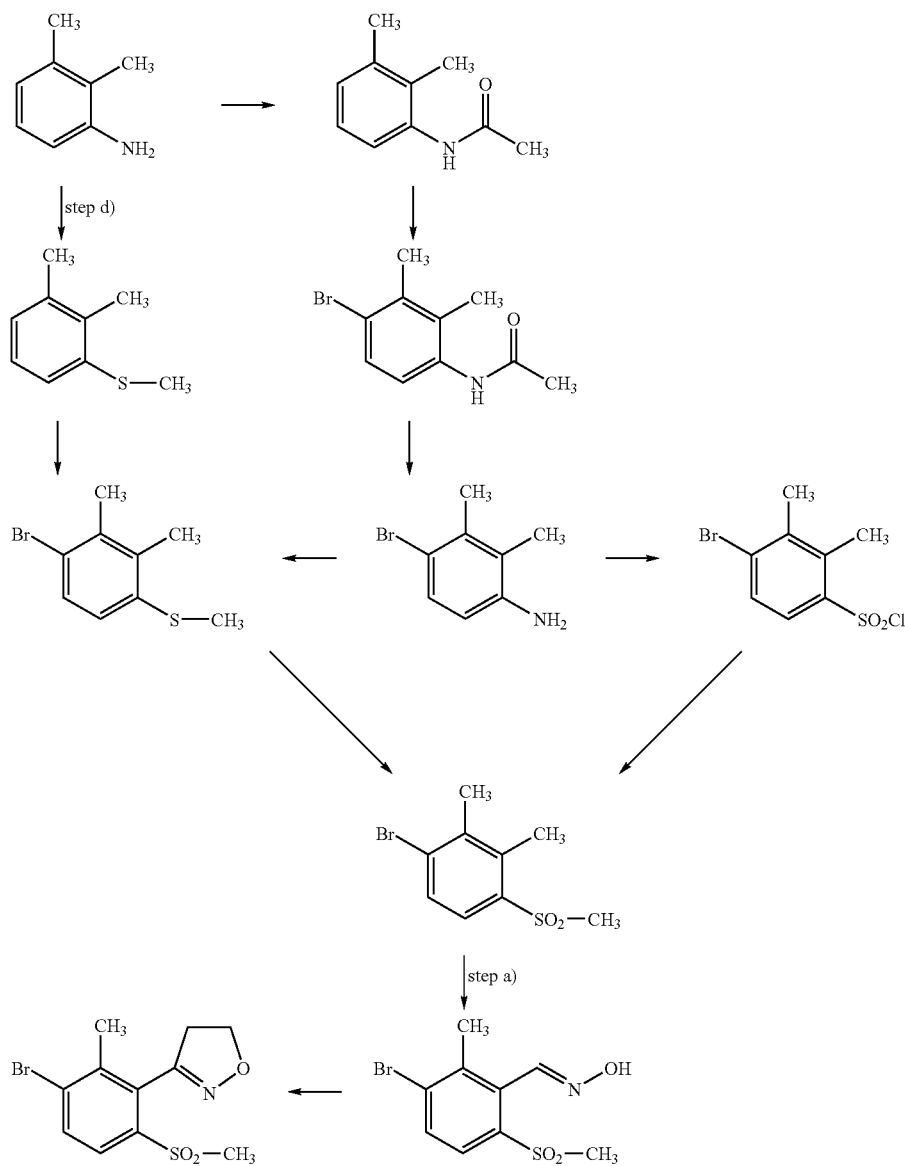

Scheme 4:

The invention is illustrated in more detail in the working examples below. Examples 1-9 relate to process steps a)-g). Examples 10-26 relate to the preparation of starting materials or intermediates, or are corresponding comparative examples. Example 27 relates to the reaction sequence for preparing compounds X, shown in scheme 4.

ture over a period of 2.5 hours. During the addition, the color of the solution changes from yellow to deep red and the solution becomes viscous. The reaction is monitored by HPLC. For work-up, initially 300 ml of water are added and then about 300 ml of glacial acetic acid, until the pH has reached 5-6. During the addition, the temperature increases to −10° C., and a yellow suspension is formed. The reaction mixture is then poured onto 6 kg of ice-water and the residue that has formed is filtered off with suction, washed with 5 l of water and dried in a drying cabinet at 30° C. overnight.

This gives 339 g of a light-beige crude product which is freed from the impurities by suspension in about 3 l of toluene at 80-90° C. for 2 hours. After cooling, the product is filtered off with suction and dried. This gives 276 g of 2-nitro-6-methyl-benzaldoxime.

Yield: 77%, m.p.: 190-192° C., purity (according to HPLC): 98%.

EXAMPLE 2

Preparation of 2-methyl-6-nitrobenzaldoxime (Process Step a)—Variant B)

1200 ml of anhydrous DMF are initially charged in a 4 l reaction flask and cooled to −40° C. At this temperature, 336.5 g (4.56 mol) of potassium methoxide (95%) are added and suspended with stirring. A mixture of 300 g (1.92 mol) of 3-nitro-o-xylene (97%) and 274 g (2.52 mol) of n-butyl nitrite (95%) is then added dropwise at −40° C. over a period of 7 hours (if the mixture is cooled accordingly, the duration of this addition can be reduced as desired; a longer period of addition has not yet been tested; temperature variations between −35 and −45° C. are tolerated). The complete conversion of the starting material is checked by HPLC. The reaction discharge is then added with stirring, at from −5 to 0° C., to a mixture of 300 ml of water and 300 ml of glacial acetic acid. The reaction mixture is then poured onto 6 kg of ice-water and the solid is separated off by filtration (without any problems, filter resistance has not yet been determined) and washed twice with in each case 500 ml of water (careful: the crude product smells strongly). The crude product (HPLC: 96 area %) is purified by suspending the moist solid in 800 ml of toluene for 1.5 h. The solid is filtered off (without any problems, the filter resistance has not yet been determined) and dried at 50° C. in a vacuum drying cabinet.

Yield: 306 g (HPLC: 99.4 area % of product; E/Z mixture), corresponds to 85% of theory.

EXAMPLE 3

Preparation of 3-(2-methyl-6-nitrophenyl)-4,5-dihydroisoxazole (Process Step b))

a) At 60° C., a small amount of a solution of 3.71 g (28 mmol) of N-chlorosuccinimide in 30 ml of acetonitrile is added to a solution of 5 g (28 mmol) of 2-methyl-6-nitrobenzaldoxime in 50 ml of acetonitrile. Once the reaction has started, the remainder of the solution is slowly added dropwise at 40-50° C. The mixture is stirred for an extra 20 minutes, until the conversion is complete by HPLC. This gives an orange solution which is carefully concentrated. The residue is suspended in 50 ml of toluene for about 1.5 hours and the solution is separated from the succinimide. The filtrate is still orange-red. The solution is filled into a mini autoclave, and an ethylene pressure of 30 bar is applied. Over a period of 5 hours, a solution of 4.7 g of sodium bicarbonate in 50 ml of water is then metered in, and the mixture is stirred at an ethylene pressure of 30 bar for another 5 hours. For work-up, the phases are separated and the toluene phase is washed 2× with NaHCO₃ solution and 1× with water, dried and concentrated. Yield: 4.9 g (86%), brownish crystals, m.p.: 100-105° C.

$^1$H-NMR (CDCl$_3$): δ=8.00 (d, 1H); 7.57 (d, 1H); 7.49 (t, 1H); 4.60 (t, 2H); 3.32 (t, 2H); 2.41 (s, 3H).

b) 100 g of 2-methyl-6-nitrobenzaldoxime are dissolved in 750 ml of glacial acetic acid, and chlorine is then introduced for 2 hours. Excess chlorine is flushed out with nitrogen. The glacial acetic acid is then distilled off and the residue is suspended in 1000 ml of toluene. The reaction mixture is filled into the autoclave, and an ethylene pressure of 6 bar is applied. Over a period of one hour, 55.6 g of triethylamine (1 equivalent) in 300 ml of toluene are metered in, and the mixture is stirred at room temperature and under 6 bar of ethylene for 10 h. The mixture is washed once with saturated aqueous NaHCO₃ solution and once with water. The organic phase is dried over sodium sulfate, filtered off and concentrated using a rotary evaporator. Yield: 96.3 g (87% of theory).

EXAMPLE 4

Preparation of 2-(4,5-dihydroisoxazol-3-yl)-3-methylaniline (Process Step c))

a) A solution of 117 g (0.57 mol) of 3-(2-methyl-6-nitrophenyl)-4,5-dihydroisoxazole in 1.2 l of ethyl acetate and 11.7 g of a catalyst containing 5% by weight of platinum on carbon are added to a hydrogenation autoclave. The autoclave is then flushed twice with nitrogen. At a hydrogen pressure of 20 bar, the mixture is then hydrogenated at 25-30° C. for 48 hours, with vigorous stirring. The reaction discharge is filtered off with suction through silica gel and the solvent is stripped off under reduced pressure. This gives 94 g of a brown solid which is taken up in methyl tert-butyl ether and water and extracted with 1M hydrochloric acid. The aqueous phase is adjusted to pH 10-11 and extracted with methylene chloride. The methylene chloride phase is dried over magnesium sulfate and the solvent is stripped off.

Yield 87 g (87%) of an orange solid, m.p.: 86-88° C., purity according to HPLC 97%.

The product can be purified further by stirring with methyl tert-butyl ether at reflux: m.p.: 90-91° C., purity according to HPLC 100%.

b) A solution of 1000 g (4.85 mol) of 3-(2-methyl-6-nitrophenyl)-4,5-dihydroisoxazole in 5.5 l of methanol and 4.6 g of a catalyst containing 10% by weight of palladium on carbon are added to a hydrogenation autoclave. The autoclave is then flushed twice with nitrogen. At a hydrogen pressure of 2.5 bar, the mixture is then hydrogenated at 25-30° C. for 17 hours, with vigorous stirring. The reaction discharge is filtered off with suction through silica gel and the solvent is stripped off under reduced pressure.

This gives 781.7 g of a light-brown solid.

Yield 781.7 g (85%) (content according to HPLC 93%).

EXAMPLE 5

Preparation of 3-(2-methyl-6-methylthiophenyl)-4,5-dihydroisoxazole (Process Step d))

19.5 g (170 mmol) of tert-butyl nitrite and 20 g of copper powder are initially charged in 30 ml of dimethyl disulfide, and a solution of 20 g (114 mmol) of 2-(4,5-dihydroisoxazol-3-yl)-3-methylaniline in 100 ml of dimethyl disulfide is added dropwise at from 50 to 55° C. The mixture is then stirred at 60° C. for 1.5 hours. For work-up, the solid is filtered off with suction and the solution is diluted with methylene chloride and extracted with dilute hydrochloric acid. The organic phase is washed with saturated aqueous NaHCO₃ solution, dried over sodium sulfate, filtered off and concentrated. Excess dimethyl disulfide is removed under oil pump vacuum.

This gives 23.4 g (99%) of a dark oil which solidifies after a while. (Content according to HPLC 100%). The product can be purified further by stirring in methyl tert-butyl ether. M.p.: 66-67° C.

EXAMPLE 6

Preparation of 3-(3-bromo-2-methyl-6-methylthiophenyl)-4,5-dihydroisoxazole (Process Step E))

At 0° C., 10 g (48 mmol) of 3-(2-methyl-6-methylthiophenyl)-4,5-dihydroisoxazole are added a little at a time to 120 ml of conc. sulfuric acid, and the mixture is stirred for about 30 minutes. 3.7 g (23 mmol) of bromine are then added dropwise, and the mixture is stirred at 0° C. for 2.5 hours. The mixture is then allowed to warm to room temperature over a period of about 45 minutes. A homogeneous solution is formed. For work-up, the reaction mixture is poured onto ice-water and extracted three times with methylene chloride. The organic phase is washed with sodium bicarbonate solution, dried with magnesium sulfate and concentrated. This gives 11.4 g of crude product which is used for the next step without further purification.

EXAMPLE 7

Preparation of 3-(3-bromo-2-methyl-6-methylsulfonylphenyl)-4,5-dihydroisoxazole (Process Step F))

At most 45° C., 11.3 g (100 mmol) of 30% strength hydrogen peroxide are added dropwise to a solution of 11.4 g (40 mmol) of 3-(3-bromo-2-methyl-6-methylthiophenyl)-4,5-dihydroisoxazole and 400 mg of sodium tungstate hydrate in 100 ml of glacial acetic acid. The reaction mixture is stirred at room temperature overnight. For work-up, the mixture is poured onto ice-water and extracted with methylene chloride, and the organic phase is washed with aqueous sodium sulfite solution, dried over magnesium sulfate and concentrated. Yield: 9.6 g. For purification, the product can be recrystallized from 65 ml of isopropanol.

Yield: 7.7 g (50% over 2 steps), m.p.: 137-139° C.

EXAMPLE 8

1-Methyl-4-(3-(4,5-dihydroisoxazol-3-yl)-2-methyl-4-methylsulfonylbenzoyl)-5-hydroxypyrazole (Process Step g)—Variant A)

2.2 l of 1,4-dioxane, 100 g (0.315 mol) of 3-(3-bromo-2-methyl-6-methylsulfonylphenyl)-4,5-dihydroisoxazole, 30.82 g (0.315 mol) of 1-methyl-5-hydroxypyrazole, 87 g (0.63 mol) of potassium carbonate, 63.5 g (0.63 mol) of triethylamine and 11.2 g (0.016 mol) of bis(triphenylphosphine)-palladium dichloride were added to a 3.5 l autoclave. The autoclave was then flushed twice with nitrogen, a carbon monoxide pressure of 10 kg/cm$^2$ was applied and the mixture was heated with stirring to 130° C. The carbon monoxide pressure was increased to 20 kg/cm$^2$ and the mixture was stirred at 130° C. for 24 h. The mixture was then concentrated under reduced pressure and the residue was taken up in water. The aqueous phase of pH 11 was extracted with dichloromethane. The organic phase is discarded. The aqueous phase is adjusted to pH 4 using 18% strength hydrochloric acid. The precipitate was filtered off, washed three times with water and dried at 40° C. under reduced pressure. This gives 85 g of product. The filtrate is extracted with dichloromethane. The organic phase is dried with sodium sulfate, and the solvent is then removed under reduced pressure, giving a further 12.7 g of product.

Yield 97.7 g (85.6%), m.p.: 215-219° C., $^1$H-NMR (CDCl$_3$): δ=2.38 (s); 3.23 (s); 3.41 (bs); 3.74 (s); 4.61 (t); 7.37 (s); 7.64 (d); 8.16 (d).

EXAMPLE 9

1-Methyl-4-(3-(4,5-dihydroisoxazol-3-yl)-2-methyl-4-methyl-sulfonylbenzoyl)-5-hydroxypyrazole (Process Step g)—Variant B)

2 l of 1,4-dioxane, 250 g (0.77 mol) of 3-(3-bromo-2-methyl-6-methylsulfonylphenyl)-4,5-dihydroisoxazole, 77 g (0.77 mol) of 1-methyl-5-hydroxypyrazole, 269 g (1.93 mol) of potassium carbonate, 197 g (1.93 mol) of triethylamine, 1.39 g (0.0077 mol) of palladium(II) chloride and 4.12 g (0.0154 mol) of triphenylphosphine were added to a 3.5 l autoclave. The autoclave was washed twice with nitrogen, the mixture was heated with stirring to 130° C. and a carbon monoxide pressure of 6 kg/cm$^2$ was applied. By continuous addition of carbon monoxide, the carbon monoxide pressure was kept constant at 6 kg/cm$^2$ and the mixture was stirred at 130° C. for 36 h. The mixture was then admixed with 1 l of demineralized water and the precipitated palladium was filtered off over a blue-band filter (pore size 2 to 3μ) and washed with water. Dioxane, triethylamine and some of the water were then distilled off in one step (150 mbar or atmospheric pressure). The aqueous phase was adjusted to pH 2.5 using 20% strength sulfuric acid and stirred at 5° C. for 12 h, while the pH was being readjusted. The precipitate was filtered off, washed three times with water and dried at 70° C. under reduced pressure. This gave 227 g of product (calc. 100%).

Yield 227 g (81%), m.p.: 215-219° C., $^1$H-NMR (CDCl$_3$): δ=2.38 (s); 3.23 (s); 3.41 (bs); 3.74 (s); 4.61 (t); 7.37 (s); 7.64 (d); 8.16 (d).

Palladium recovery rate on filter: 85-98%

Elemental analysis of the palladium that was filtered off (dried): Pd 48%, O 22%, C 11%, H 1.3%, P 0.2%, S 0.2%, Br<0.5%, Cl<0.5%, N<0.5%.

EXAMPLE 10

Preparation of 4-bromo-2-(4,5-dihydroisoxazol-3-yl)-3-methylaniline 30 g (170 mmol) of 2-(4,5-dihydroisoxazol-3-yl)-3-methylaniline are dissolved in 400 ml of acetonitrile, and 94 g (0.68 mol) of potassium carbonate are added. At temperatures <30° C., 84 g (174 mmol) of tetrabutylammonium tribromide are then added a little at a time, with vigorous stirring. For work-up, the solid is filtered off with suction and the solution is diluted with methylene chloride and extracted with water. The solvent is stripped off and the residue is then taken up again in methyl tert-butyl ether and washed twice with water. The organic phase is dried and concentrated.

Yield 20.4 g (47%) of a brown solid, m.p.: 126-130° C., purity according to HPLC 97%

EXAMPLE 11

Preparation of 4-bromo-2-(4,5-dihydroisoxazol-3-yl)-3-methyl-benzenesulfonyl chloride At 15° C., a solution of 9 g (35 mmol) of 4-bromo-2-(4,5-dihydro-isoxazol-3-yl)-3-methylaniline in 50 ml of glacial acetic acid is added to 15 ml of conc. hydrochloric acid. At 5-10° C., a solution of 2.44 g (35 mmol) of sodium nitrite in 10 ml of water is then added dropwise, and the mixture is stirred at 5° C. for 1 hour. This solution is then added dropwise at room temperature to a mixture of a solution of 47 g (0.74 mol) of sulfur dioxide in 100 ml of glacial acetic acid and a solution of 2.23 g (13 mmol) of copper(II) chloride in 5 ml of water. The mixture is stirred at room temperature for 1 hour and then poured onto 300 ml of ice-water and extracted with methylene chloride. The organic phase is washed with water, dried with magnesium sulfate and concentrated.

Yield 11.8 g (99%), purity according to HPLC 96%

In the working examples below, the preparation of benzaldoximes of the formula XV (process step a) is described in more detail.

EXAMPLE 12

Preparation of 2-methyl-6-nitrobenzaldoxime (Variant A)

A solution of 274 g (2.6 mol) of n-butyl nitrite (97%) and 300 g (2.0 mol) of 3-nitro-o-xylene (97%) in 750 ml of dimethylformamide is cooled to from −55 to −60° C., and a solution of 522 g (4.56 mol) of potassium tert-butoxide in 750 ml of dimethylformamide is added dropwise at this temperature over a period of 2.5 hours. During the addition, the color of the solution changes from yellow to deep red and the solution becomes viscous. The reaction is monitored by HPLC. For work-up, initially 300 ml of water are added and then about 300 ml of glacial acetic acid, until the pH has reached 5-6. During the addition, the temperature increases to −10° C., and a yellow suspension is formed. The reaction mixture is then poured onto 6 kg of ice-water and the residue that has formed is filtered off with suction, washed with 5 l of water and dried in a drying cabinet at 30° C. overnight. This gives 339 g of a light-beige crude product which is freed from the impurities by suspension in about 3 l of toluene at 80-90° C. for 2 hours. After cooling, the product is filtered off with suction and dried. This gives 276 g of 2-nitro-6-methyl-benzaldoxime.

Yield: 77%, m.p.: 190-192° C., purity (according to HPLC): 98%.

EXAMPLE 13

Preparation of 2-methyl-6-nitrobenzaldoxime (Variant B)

1200 ml of anhydrous DMF are initially charged in a 4 l reaction flask and cooled to −40° C. At this temperature, 336.5 g (4.56 mol) of potassium methoxide (95%) are added and suspended with stirring. A mixture of 300 g (1.92 mol) of 3-nitro-o-xylene (97%) and 274 g (2.52 mol) of n-butyl nitrite (95%) is then added dropwise at −40° C. over a period of 7 hours (if the mixture is cooled accordingly, the duration of this addition can be reduced as desired). The complete conversion of the starting material is checked by HPLC. The reaction discharge is then added with stirring, at from −5 to 0° C., to a mixture of 300 ml of water and 300 ml of glacial acetic acid. The reaction mixture is then poured onto 6 kg of ice-water and the solid is separated off by filtration and washed twice with in each case 500 ml of water.

The crude product (HPLC: 96 area %) is purified by suspending the moist solid in 800 ml of toluene for 1.5 h. The solid is filtered off and dried at 50° C. in a vacuum drying cabinet.

Yield: 306 g (HPLC: 99.4 area % of product; E/Z mixture), corresponds to 85% of theory.

EXAMPLE 14

Preparation of 2-chloro-6-nitrobenzaldoxime

A solution of 4.1 g (40 mmol) of n-butyl nitrite (97%) and 5 g (29 mmol) of 2-chloro-6-nitrotoluene in 50 ml of dimethyl-formamide is cooled to from −55 to −60° C., and a solution of 3.3 g (29.5 mmol) of potassium tert-butoxide in 30 ml of dimethylformamide is added dropwise at this temperature, over a period of 20 minutes. The reaction is monitored by HPLC. For work-up, initially water is added, and the solution is then adjusted to pH 5-6 using glacial acetic acid. The product is isolated by extraction with ethyl acetate. This gives 5.7 g of 2-chloro-6-nitrobenzaldoxime. $^1$H-NMR (CDCl$_3$): δ=8.00 (d, 1H); 7.84 (s, 1H); 7.76 (d, 1H); 7.52 (t, 1H).

EXAMPLE 15

Preparation of 3-chloro-2-methyl-6-methylsulfonylbenzaldoxime

A solution of 12.7 g (119 mmol) of n-butyl nitrite (97%) and 20 g (92 mmol) of 2,3-dimethyl-4-methylsulfonylchlorobenzene in 100 ml of dimethylformamide is cooled to from −55 to −60° C., and a solution of 16.8 g (147 mmol) of potassium tert-butoxide in 70 ml of dimethylformamide is added dropwise at this temperature, over a period of 30 minutes. The reaction is monitored by HPLC. For work-up, initially 50 ml of water are added, and the mixture is then adjusted to pH 5-6 using about 30 ml of glacial acetic acid. The mixture is then poured onto 0.7 kg of ice-water and the aqueous phase is extracted with methylene chloride. The organic phase is washed with sodium bicarbonate solution, dried over magnesium sulfate and concentrated. This gives 18.4 g of a light-beige crude product which is purified by recrystallization from about 30 ml of toluene.

Yield: 6.15 g (27%) of white crystals, m.p.: 164-168° C., purity (according to HPLC): 100%

EXAMPLE 16

Preparation of 3-bromo-2-methyl-6-methylsulfonylbenzaldoxime

A solution of 2.1 g (20 mmol) of n-butyl nitrite (97%) and 4 g (15 mmol) of 2,3-dimethyl-4-methylsulfonylbromobenzene in 50 ml of dimethylformamide is cooled to from −55 to −60° C., and a solution of 2.8 g (25 mmol) of potassium tert-butoxide in 35 ml of dimethylformamide is added dropwise at this temperature, over a period of 20 minutes. The reaction is monitored by HPLC. For work-up, initially 10 ml of water are added, and the mixture is then adjusted to pH 5-6 using about 9 ml of glacial acetic acid. The mixture is then poured onto 100 ml of ice-water and the aqueous phase is extracted with methylene chloride. The organic phase is washed with sodium bicarbonate solution, dried over magnesium sulfate and concentrated. This gives 3.6 g of an oily crude product (90% by HPLC) which can be purified by recrystallization from toluene.

Yield: 1.22 g (27%), m.p.: 192-194° C., purity (according to HPLC): 99%

EXAMPLE 17

Preparation of N,N-diphenyl-3-hydroxyamino-2-methyl-4-methyl-sulfonylbenzamide a) Preparation of the Precursor

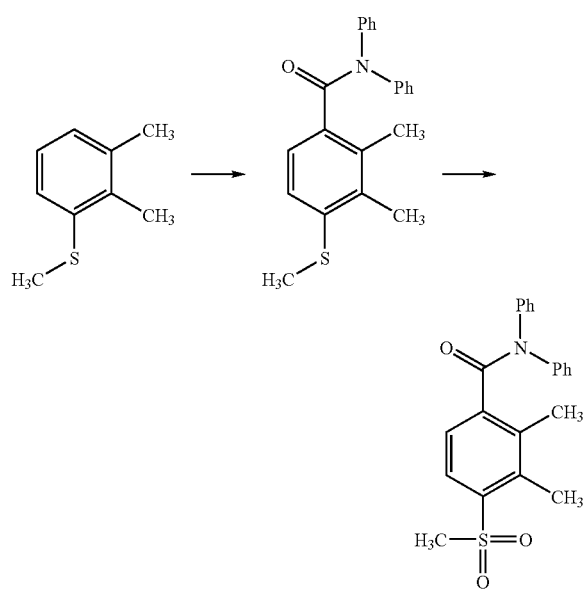

5 g (3 mmol) of 2,3-dimethylthioanisole and 7.6 g (33 mmol) of diphenylcarbamoyl chloride are dissolved in 50 ml of 1,2-dichloroethane and, at room temperature, admixed with 4.8 g (36 mmol) of anhydrous aluminum chloride. The reaction mixture is boiled at reflux for 3 hours and then poured onto a mixture of ice and concentrated hydrochloric acid, and the aqueous phase is extracted twice with methylene chloride. The organic phase is washed with sodium bicarbonate solution, dried over magnesium sulfate and concentrated. This gives 10.8 g of crude product which is purified by silica gel chromatography using the mobile phase toluene/ethyl acetate. Yield: 7.8 g of N,N-diphenyl-2,3-dimethyl-4-methylthio-benzamide.

At most 45° C., 5.7 g (50 mmol) of 30% strength hydrogen peroxide are added dropwise to a solution of 7 g (20 mmol) of N,N-diphenyl-2,3-dimethyl-4-methylthiobenzamide and 200 mg of sodium tungstate hydrate in 50 ml of glacial acetic acid. The mixture is stirred at room temperature overnight. For work-up, the mixture is poured onto ice-water and extracted with methylene chloride, and the organic phase is washed with aqueous sodium sulfite solution, dried over magnesium sulfate and concentrated.

Yield: 7.4 g of N,N-diphenyl-2,3-dimethyl-4-methylsulfonyl-benzamide, m.p.: 155-165° C.

b) Preparation of N,N-diphenyl-3-hydroxyimino-2-methyl-4-methylsulfonyl-benzamide A solution of 0.7 g (6.9 mmol) of n-butyl nitrite (97%) and 2 g (5.3 mmol) of N,N-diphenyl-2,3-dimethyl-4-methylsulfonyl-benzamide in 30 ml of dimethylformamide is cooled to from −55 to −60° c, and a solution of 1.4 g (12 mmol) of potassium tert-butoxide in 10 ml of dimethylformamide is added dropwise at this temperature, over a period of 20 minutes. The reaction is monitored by HPLC. For work-up, initially 10 ml of water are added, and the mixture is then adjusted to pH 5-6 using glacial acetic acid. The mixture is then poured onto 100 ml of ice-water and the aqueous phase is extracted with ethyl acetate. The organic phase is washed with sodium bicarbonate solution, dried over magnesium sulfate and concentrated. This gives 3.0 g of a partially crystalline crude product, which is purified by silica gel chromatography using the mobile phase toluene/acetone.

Yield: 1.0 g (46%), m.p.: 208-211° C.

EXAMPLE 18

Preparation of 3-bromo-2-methyl-6-methylsulfonylbenzaldehyde 7.1 g of 3-bromo-2-methyl-6-methylsulfonylbenzaldoxime (23 mmol) are stirred at 65° C. in a mixture of 17 g of 5% strength hydrochloric acid, 2 g of 37% strength formaldehyde solution, 15 ml of water and 30 ml of tetrahydrofuran for 32 hours. During this time, a further 3.5 g of 37% strength formaldehyde solution are added in portions of 0.5 g. The mixture is then cooled to room temperature and the product is filtered off with suction.

This gives 5.1 g (79%) of product, purity 94% (according to GC).

EXAMPLE 19

Preparation of 2-methyl-6-nitrobenzaldehyde

At 65° C., 14 g of 2-methyl-6-nitrobenzaldoxime (80 mmol) are stirred in a mixture of 55 ml of 5% strength hydrochloric acid, 37 g of 37% strength formaldehyde solution, 50 ml of water and 100 ml of tetrahydrofuran for 24 hours. The phases are then separated and the dark phase is extracted with methylene chloride/water. The organic phase is dried with sodium sulfate and concentrated. This gives 10.1 g of crude product, which is purified by filtration through silica gel using the mobile phase toluene.

Yield: 7.2 g (54%)

EXAMPLE 20

Preparation of 2-methyl-6-nitrobenzonitrile

35 A solution of 16 g (150 mmol) of n-butyl nitrite (97%) and 7.7 g (50 mmol) of 3-nitro-o-xylene (97%) in 50 ml of dimethylformamide is cooled to from −5 to −10° C., and a solution of 11 g (100 mmol) of potassium tert-butoxide in 50 ml of dimethylformamide is added at this temperature, over a period of 1.5 hours. The reaction mixture is stirred at room temperature for another 6 days. For work-up, the mixture is poured onto ice-water and adjusted to pH 1 using hydrochloric acid, and the aqueous phase is extracted with ethyl acetate. The organic phase is washed with water, dried over magnesium sulfate and concentrated. This gives 8.2 g of product. The 2-methyl-6-nitrobenzonitrile can be purified by silica gel chromatography using the mobile phase toluene. M.p.: 101-103° C.

In the working examples below, the preparation of thioethers of the formula VIIIa (process step d) is described in more detail:

EXAMPLE 21 a) Comparative Example

The reaction of 2,3-dimethylaniline with dimethyl disulfide and tert-butyl nitrite in the solvent methylene chloride gives only a small amount of the desired product C. According to GC analysis, the main products were the dimerization products A and B. The dimer A is also formed if the reaction is carried out in excess dimethyl disulfide.

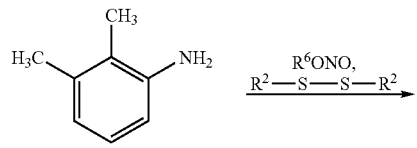

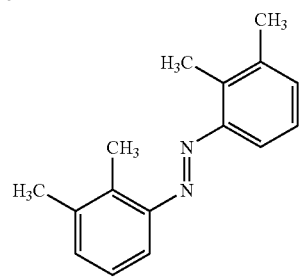

A

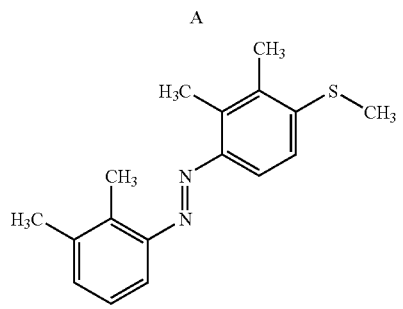

B

C b) Process According to the Invention

The reaction of 2,3-dimethylaniline with dimethyl disulfide and tert-butyl nitrite is carried out similarly to the method described in a) using the solvent methylene chloride, but Cu powder is additionally added as catalyst. The reaction proceeds uniformly to give the desired dimethylthioanisole C. It was not possible to identify the dimerization product A and B by GC analysis.

EXAMPLE 22 a) Comparative Example

In the reaction of 2-(4,5-dihydroisoxazol-3-yl)-3-methylaniline with dimethyl disulfide and tert-butyl nitrite without catalyst, byproducts are formed. A mixture of A and B in a ratio of 2:1 according to HPLC area percent is obtained.

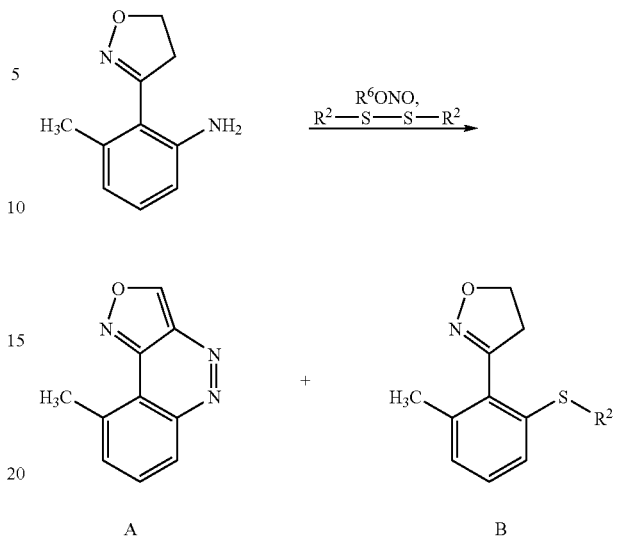

A                B b) Process According to the Invention

The reaction is carried out similarly to the method described in a), but in the presence of Cu powder. In this case, the byproduct A cannot be detected.

EXAMPLE 23

Preparation of 2,3-dimethylthioanisole a) 355 g (3.44 mol) of tert-butyl nitrite and 250 g of copper powder (3.9 mol) are initially charged in 1250 ml of dimethyl disulfide, and a solution of 250 g (2.07 mol) of 2,3-dimethylaniline in 1000 ml of dimethyl disulfide is added dropwise at 50-52° C. The mixture is subsequently stirred at 75-80° C. for 1.5 hours. For work-up, the mixture is cooled, filtered off with suction through kieselguhr, and the filtrate is washed with saturated aqueous $NaHCO_3$ solution. For the purification of the product, the organic phase is separated by distillation. Initially, excess dimethyl disulfide is removed at atmospheric pressure. 1446 g of dimethyl disulfide (purity >97% according to GC) are recovered. The residue is then subjected to fractional distillation under reduced pressure (0.1 mbar).

Yield: 261.3 g (83%), purity according to GC 97.5% b) 14.2 g (124 mmol) of tert-butyl nitrite and 2.5 g (40 mmol) of copper powder are initially charged in 50 ml of dimethyl disulfide, and a solution of 10 g (81 mmol) of 2,3-dimethylaniline in 50 ml of dimethyl disulfide is added dropwise at 50-52° C. The mixture is subsequently stirred at 75-80° C. for 1.5 hours. According to GC analysis, 100% of the aniline has been converted into the desired 2,3-dimethylthioanisole.

EXAMPLE 24

Preparation of 2-methyl-6-nitrothioanisole 226 g (1.97 mmol) of tert-butyl nitrite and 100 g of copper powder are initially charged in 300 ml of dimethyl disulfide, and a solution of 200 g (1.32 mol) of 2-methyl-6-nitroaniline in 700 ml of dimethyl disulfide is added dropwise at 50-55° C. The mixture is then stirred at 75° C. for 8 hours. For work-up, the solid is filtered off with suction and the solution is diluted with methylene chloride and extracted with dilute hydrochloric acid. The organic phase is washed with saturated aqueous NaHCO$_3$ solution, dried over sodium sulfate, filtered off and concentrated using a rotary evaporator. Excess dimethyl disulfide is removed under oil pump vacuum. This gives 271 g (99%) of a dark-red oil, purity according to HPLC 87%.

EXAMPLE 25

Preparation of 2-methyl-3,4-dimethylthiobromobenzene 14.8 g (129 mmol) of tert-butyl nitrite and 20 g of copper powder are initially charged in 50 ml of dimethyl disulfide, and a solution of 20 g (86 mol) of 4-bromo-3-methyl-2-methylthioaniline in 100 ml of dimethyl disulfide is added dropwise at 50-55° C. The mixture is then stirred at 50° C. for 4 hours. For work-up, the solid is filtered off with suction and the solution is diluted with methylene chloride and extracted with dilute hydrochloric acid. The organic phase is washed with saturated aqueous NaHCO$_3$ solution, dried over sodium sulfate, filtered off and concentrated using a rotary evaporator. Excess dimethyl disulfide is removed under oil pump vacuum.

This gives 19.7 g of a dark oil. The product can be purified by trituration in methyl tert-butyl ether.

Yield 9.32 g (41%), m.p.: 70-73° C.

EXAMPLE 26

Preparation of 2,3-dimethyl-4-methylthiobromobenzene 603 g (5.85 mol) of tert-butyl nitrite and 375 g of copper powder (5.9 mol) are initially charged in 3000 ml of dimethyl disulfide, and 761 g (3.75 mol) of 4-bromo-2,3-dimethylaniline are added dropwise at 50-58° C. The mixture is then stirred at 75-80° C. for 9 hours. For work-up, the mixture is cooled, the residue is filtered off and the filtrate is washed with saturated aqueous NaHCO$_3$ solution. For purification of the product, the organic phase is separated by distillation. Initially, excess dimethyl disulfide is removed under atmospheric pressure. 1870 g of dimethyl disulfide (purity >97% according to GC) are recovered. The residue is then subjected to fractional distillation under reduced pressure (0.1 mbar).

Yield: 523 g (60%), purity according to GC 99%.

EXAMPLE 27

(Reaction Sequence According to Scheme 4)

a) Preparation of 2,3-dimethylthioanisole 355 g (3.44 mol) of tert-butyl nitrite and 250 g of copper powder (3.9 mol) are initially charged in 1250 ml of dimethyl disulfide, and a solution of 250 g (2.07 mol) of 2,3-dimethylaniline in 1000 ml of dimethyl disulfide is added dropwise at 50-52° C. The mixture is subsequently stirred at 75-80° C. for 1.5 hours. For work-up, the mixture is cooled, filtered off with suction through kieselguhr, and the filtrate is washed with saturated aqueous NaHCO$_3$ solution. For the purification of the product, the organic phase is separated by distillation. Initially, excess dimethyl disulfide is removed at atmospheric pressure. 1446 g of dimethyl disulfide (purity >97% according to GC) are recovered. The residue is then subjected to fractional distillation under reduced pressure (0.1 mbar).

Yield: 261.3 g (83%), purity (according to GC) 97.5% b) Preparation of 2,3-dimethyl-4-methylthiobromobenzene 510 g (3.33 mol) of 2,3-dimethylthioanisole are initially charged in 3 l of glacial acetic acid, and a solution of 592 g (7.4 mol) of bromine in 1 l of glacial acetic acid is added dropwise at room temperature over a period of three hours. The reaction is slightly exothermic. The reaction mixture is stirred at room temperature for another 3.5 hours. The precipitate is then filtered off with suction and the filtrate is admixed with 270 g of sodium acetate and concentrated. The residue is taken up in 2 l of dichloromethane and washed twice with 2 l of sodium bicarbonate solution and twice with sodium chloride solution.

The organic phase is dried over sodium sulfate and concentrated.

Yield: 615 g (79%), purity (according to GC) 99.2%.

c) Preparation of 2,3-dimethyl-4-methylsulfonylbromobenzene

At most 100° C. (slight reflux), 266 g (2.35 mol) of 30% strength hydrogen peroxide are added dropwise over a period of 45 minutes to a solution of 182 g (0.78 mol) of 2,3-dimethyl-4-methylthiobromobenzene and 5.24 g of sodium tungstate hydrate in 1 l of glacial acetic acid. The reaction mixture is stirred at room temperature for another two hours. For work-up, the mixture is poured onto 7.8 l of ice-water and stirred for another 30 minutes. The white residue is then filtered off with suction and washed three times with water. The crystals are dried at 70° C. under reduced pressure overnight.

Yield: 195 g (94%), purity (according to GC) 100%.

d) Preparation of 3-bromo-2-methyl-6-methylsulfonylbenzaldoxime 272.6 g of sodium ethoxide (3.8 mol) are dissolved in 0.4 l of DMF, and a solution of 400 g of 2,3-dimethyl-4-methylsulfonylbromobenzene (1.52 mol) and 214.6 g (1.977 mol) of n-butyl nitrite in 0.8 l of DMF is added at from −20° C. to −15° C. Subsequently, another 100 g of sodium ethoxide are added. The reaction mixture is stirred at from −20° C. to −15° C. for a total of 5.5 hours.

The mixture is poured onto 4 l of ice-water and 0.4 l of glacial acetic acid and extracted with a total of 4 l of MtBE. The MtBE phase is washed with 1 l of sodium bicarbonate solution and twice with water. The aqueous phases are combined. The MtBE phase is concentrated using a rotary evaporator and dried. The solution is concentrated and the residue is dried using an oil pump.

Yield: 331 g (75%) of yellow-brown crystals, purity (according to HPLC) 96.6%.

e) Preparation of 3-(3-bromo-2-methyl-6-methylsulfonylphenyl)-4,5-dihydro-isoxazole At 60° C., a small amount of N-chlorosuccinimide is added to a solution of 50 g (171 mmol) of 3-bromo-2-methyl-6-methyl-sulfonylbenzaldoxime in 200 ml of dimethylformamide. Once the reaction has started, a total of 23.3 g (171 mmol) of N-chlorosuccinimide are metered in at 40-50° C. The reaction mixture is stirred for another 30 minutes, until conversion is complete according to HPLC. The reaction mixture is then poured onto ice-water and the solid is filtered off with suction, washed three times with water and twice with n-pentane. The hydroxamic acid chloride is used moist and without further purification for the next reaction. The solid is dissolved in 250 ml of dichloromethane, and ethylene is passed through the solution. With continued introduction of ethylene, 20.3 g (200 mmol) of triethylamine are added dropwise. The reaction mixture is stirred at room temperature for about 72 hours, with repeated introduction of more gaseous ethylene.

For work-up, the reaction mixture is washed three times with water, and the solvent is stripped off. This gives 49 g of brownish crystals which, according to HPLC, contain 90.6% of product. The product can be purified by recrystallization from 200 ml of isopropanol.

Yield: 31 g (57%) of white crystals, m.p.: 133-136° C., purity (according to HPLC) 99.5%.

We claim:

1. A process for preparing a compound of formula XV

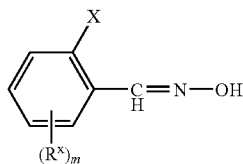

in which

X is $NO_2$ or $S(O)_n R^y$, $R^x$ is halogen, carboxyl, carboxamide, N-alkyl-carboxamide, N,N-dialkylcarboxamide, phenyl, $C_1$-$C_6$-alkyl, $C_1$-$C_6$-alkoxy or $C_1$-$C_6$-alkylthio, $R^y$ is $C_1$-$C_6$-alkyl;

m is 1, 2, 3 or 4, and n is 2, or a corresponding aldehyde, nitrile or nitrile oxide, which comprises reacting a compound of the formula XVI

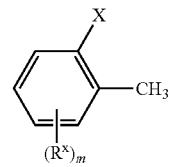

in which X and $(R^x)_m$ are as defined above, with an organic nitrite of the formula R—O—NO, where R is an aliphatic or aromatic radical, in the presence of a base, to obtain the compound of the formula XV, and optionally converting the oxime group —CH=NOH in formula XV into an aldehyde moiety (—CHO), a nitrile (—CN) or a nitrile oxide (—CHO), wherein the reaction is carried out at a temperature below −20° C. in the presence of a dipolar aprotic solvent.

2. A process as claimed in claim 1, wherein the compound of formula XVI is reacted in the presence of DMF.

3. The process of claim 1, wherein $R^x$ is halogen, carboxyl, carboxamide, N-alkyl-carboxamide, N,N-dialkylcarboxamide, phenyl, $C_1$-$C_6$-alkyl, $C_1$-$C_6$-alkoxy or $C_1$-$C_6$-alkylthio, wherein a first group $R^x$ is bonded to the phenyl ring in ortho position relative to the CH=N—OH moiety and denotes $C_1$-$C_6$-alkyl, halogen, $C_1$-$C_6$-alkoxy or $C_1$-$C_6$-alkylthio;

$R^y$ is $C_1$-$C_6$-alkyl, and m is 2.

* * * * *